US006313168B1

(12) United States Patent
Pacifici et al.

(10) Patent No.: US 6,313,168 B1
(45) Date of Patent: Nov. 6, 2001

(54) USE OF RETINOID RECEPTOR ANTAGONISTS IN THE TREATMENT OF CARTILAGE AND BONE PATHOLOGIES

(75) Inventors: Maurizio Pacifici, Swarthmore, PA (US); Roshantha A. Chandraratna, Laguna Hills, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/464,344

(22) Filed: Dec. 15, 1999

(51) Int. Cl.$^7$ ............................ A61K 31/35; A61K 31/07

(52) U.S. Cl. ............................................ 514/546; 514/725

(58) Field of Search ..................................... 514/456, 725

(56) References Cited

U.S. PATENT DOCUMENTS

| | | |
|---|---|---|
| 5,514,825 | 5/1996 | Vuligonda et al. . |
| 5,648,514 | 7/1997 | Johnson et al. . |
| 5,728,846 | 3/1998 | Vuligonda et al. . |
| 5,739,338 | 4/1998 | Beard et al. . |
| 5,760,276 | 6/1998 | Beard et al. . |
| 5,763,635 | 6/1998 | Vuligonda et al. . |
| 5,773,594 | 6/1998 | Johnson et al. . |
| 5,776,699 | 7/1998 | Klein et al. . |
| 5,808,124 | 9/1998 | Beard et al. . |
| 5,877,207 | 3/1999 | Klein et al. . |

FOREIGN PATENT DOCUMENTS

WO 93/11755    6/1993 (WO) .

OTHER PUBLICATIONS

Derwent Abstract 1998—316746.*
Jacenko et al, "Transgenic Mouse Models in Studies of Skeletal Disorders", J. Rheumatol. 22: 39–41 (1995).
Coffin et al, "Abnormal Bone Growth and Selective Translational Regulation in Basic Fibroblast Growth Factor (FGF–2) Transgenic Mice", Mol. Biol. Cell, 6: 1861–1873(1995).
Colvin et al, "Skeletal overgrowth and deafness in mice lacking fibroblast growth factor receptor 3", Nature Genet, 12: 390–397(1996).
Vortkamp et al, "Regulation of Rate of Cartilage Differentiation by Indian Hedgehog and PTH–Related Protein" Science, 273: 613–622 (1996).
Hamerman, "The Biology of Osteoarthritis", New Engl. J. Med. 320 (20), 1322–1330 (1989).
von der Mark et al, "Upregulation of type X collagen expression in osteoarthritic cartilage", Acta Orthop. Scand., (Suppl 266) 125–129 (1995).
Robbins et al, "Bones", Pathological Basis of Disease, W.B. Saunders Co. (1979); 1477–1513.
Koyama et al, "Retinoid Signaling Is Required for Chondrocyte Maturation and Endochondral Bone Formation during Limb Skeletogenesis", Develop. Biol. 208(2):375–391 (1999).

Noji et al, "Expression Pattern of the Homeobox Gene HOX–3.5 During Mouse Development, as Revealed by a Simplified In Situ Hybridization Method", Acta Histochem, Cytochem. 23(3): 353–366 (1990).
Koyama et al, "Syndecan–3, Tenascin–C, and the Development of Cartilaginous Skeletal Elements and Joints in Chick Limbs", Dev. Dynam. 203: 152–162 (1995).
Noji et al, "Retinoic acid induces polarizing activity but is unlikely to be a morphogen in the chick limb bud", Nature 350: 83–86 (1991).
Michaille et al, "Characterization of cDNAs Encoding the Chick Retinoic Acid Receptor γ2 and Preferential Distribution of Retinoic Acid Receptor γ Transcripts During Chick Skin Development", 334 Dev. Dynam. 201: –343 (1994).
Bennett et al, "Cartilage–specific 5' End of Chick α2(I) Collagen mRNAs*", J. Biol. Chem. 264 (14): 8402–8409 (1989).
Leboy et al, "Ascorbic Acid Induces Alkaline Phosphatase, Type X Collagen, and Calcium Deposition in Cultured Chick Chondrocytes*", J. Biol. Chem. 264 (29): 17281–17286 (1989).
Young et al, "Isolation of cDNA and genomic DNA clones encoding type II collagen", Nucl. Acids Res. 12 (10); 4207–4228.
Apfel et al, "A retinoic acid receptor α antagonist selectively counteracts retinoic acid effects", Proc. Natl. Acad. Sci. 89: 7129–7133 (1992).
Keidel et al., "Different Agonist– and Antagonist–Induced Conformational Changes in Retinoic Acid Receptors Analyzed by Protease Mapping", Mol. Cell. Biol. 14(1): 287–298 (1994).
Klein et al, "Identification and Functional Separation of Retinoic Acid Receptor Neutral Antagonists and Inverse Agonists*", J. Biol. Chem. 271 (37): 22692–22696 (1996).
Lu et al, "Retinoid signaling is required for the establishment of a ZPA and for the expression of Hoxb–8, a mediator of ZPA formation", Development 124: 1643–1651 (1997).
Hamburger et al, "A Series of Normal Stages in the Development of the Chick Embryo", J. Morphol. 88: 49–92 (1951).
Gibson et al, "Type X Collagen Synthesis by Chick Sternal Cartilage and Its Relationship to Endochondral Development", J. Cell Biol. 101: 277–284 (1985).
Pacifici et al, "Retinoic Acid Treatment Induces Type X Collagen Gene Expression in Cultured Chick Chondrocytes", Exp. Cell Res. 195: 38–46 (1991).
Iwamoto et al, "Retinoic Acid Induces Rapid Mineralization and Expression of Mineralization–Related Genes in Chondrocytes", Exp. Cell Res. 207: 413–420 (1993b).

(List continued on next page.)

*Primary Examiner*—Zohreh Fay

(57) ABSTRACT

The present invention relates to methods for treating cartilage and bone pathologies, including bone growth related diseases such as osteoarthritis, comprising administering therapeutically effective amounts of retinoid receptor antagonists.

42 Claims, No Drawings

OTHER PUBLICATIONS

Chomczynski et al, "Single–Step Method of RNA Isolation by Acid Guanidinium Thiocyanate–Phenol–Chloroform Extraction", Anal. Biochem. 162: 156–159 (1987).

Oettinger et al, "Type X Collagen Gene Expression Is Transiently Up–Regulated by Retinoic Acid Treatment in Chick Chondrocyte Cultures", Exp. Cell Res. 191: 292–298 (1990).

Iwamoto et al, "Responsiveness to Retinoic Acid Changes during Chondrocyte Maturation", Exp. Cell Res. 205: 213–224 (1993a).

Wagner et al, "Regional differences in retinoid release from embryonic neural tissue detected by an in vitro reporter assay", Development 116: 55–66 (1992).

McCaffery et al, "Asymmetrical retinoic acid synthesis in the dorsoventral axis of the retina" Development 115: 371–382 (1992).

Ellis et al, "Phosphorylation of GAP and GAP–associated proteins by transforming and mitogenic tyrosine kinases", Nature 343: 377–381 (1990).

Zelent et al, "Cloning of murine α and β retinoic acid receptors and a novel receptor γ predominantly expressed in skin", Nature 339: 714–717 (1989).

Levin et al, "9–Cis retinoic acid stereoisomer binds and activates the nuclear receptor RXRα" Nature 355: 359–361 (1992).

Lim et al, "A Simple Assay for DNA Transfection by Incubation of the Cells in Culture Dishes with Substrates for Beta–Galactosidase", Biotechniques 7 (6), 576–579 (1989).

Fell, "The Histogenesis of Cartilage and Bone in the Long Bones of the Embryonoic Fowl", J. Morphol. Physiol. 40: 417–459 (1925).

Scott–Savage et al, "The Timing of the Onset of Osteogenesis in the Tibia of the Embryonic Chick", J. Morphol 162: 453–464 (1979).

Osdoby et al, "First Bone Formation in the Developing Chick Limb", Dev. Biol. 86: 147–156 (1981).

Koyama et al,: "Early Chick Limb Cartilaginous Elements Possess Polarizing Activity and Express Hedgehog–Related Morphogenetic Factors", Dev. Dynam. 207344–354 (1996).

Iwamoto et al, "Retinoic Acid Is a Major Regulator of Chondrocyte Maturation and Matrix Mineralization", Microsc. Res. Tech. 28: 483–491 (1994).

Nerlich et al, "Immunohistochemical analysis of interstitial collagens in cartilage of different stages of osteoarthrosis", Vichows Archiv. B. Cell Pathol. 63, 249–255 (1993).

Weston et al, "Regulation of Skeletal Progenitor Differentiation by the BMP and Retinoid Signaling Pathways", The Journal of Cell Biology, vol. 148, (4), 679–690 (2000).

* cited by examiner

USE OF RETINOID RECEPTOR ANTAGONISTS IN THE TREATMENT OF CARTILAGE AND BONE PATHOLOGIES

BACKGROUND OF THE INVENTION

Articular cartilage is a unique tissue present in the joints in the limbs, trunk and cervical region. The tissue is composed of articular chondrocytes and an abundant extracellular matrix that contains several well characterized macromolecules, including proteoglycan aggregates, hyaluronic acid, link protein and type II collagen fibrils. The chondrocytes are responsible for the synthesis, deposition and maintenance of the matrix components. The proteoglycan aggregates are large supramolecular structures that bind large quantities of water molecules and ions and provide the tissue with bioelasticity. The collagen fibrils form a three dimensional network that is able to withstand tensile and shear forces and provides the tissue with tensile strength. Together, the proteoglycan aggregates and collagen fibrils are responsible for a fundamental biomechanical property of articular cartilage, resilience. This property allows the tissue to undergo reversible changes in shape and volume that result from physical forces acting on the joints during movement, and thus permit normal functioning of the joints. Under normal healthy circumstances, articular chondrocytes remain active and phenotypically stable throughout life; in turn, this allows articular cartilage to maintain its structural and organization characteristics and to perform its biomechanical roles in the joints throughout life.

Endochondral ossification is the process by which the cartilaginous skeletal elements present in the embryo and growing organism are replaced by definitive bone elements. The process starts in the second half of embryogenesis and is concluded at the end of puberty when skeletal growth ceases. Endochondral ossification is a highly-regulated multistep process that involves several distinct steps of chondrocyte maturation and is best appreciable in long bone growth plates in the limbs. During endochondral ossification, resting immature chondrocytes first undergo a phase of rapid cell proliferation. The cells then withdraw from the cell cycle and enter a phase of active matrix production. Matrix components synthesized at this step are typical cartilage matrix macromolecules, including proteoglycans (aggrecan), type II collagen, link protein and hyaluronan. The postmitotic matrix-synthesizing cells then begin to enlarge in size and change from flat to oval-round in shape. This step is called the pre-hypertrophic stage and is characterized by synthesis of new proteins, including the signaling factor Indian hedgehog. The cells continue to enlarge and advance to their ultimate stage of maturation, the hypertrophic stage. The biosynthetic repertoire of hypertrophic chondrocytes changes dramatically, and the cells initiate production of various new proteins including: metalloproteases, type X collagen, alkaline phosphatase and annexin V-rich matrix vesicles. As they undergo these changes in biosynthesis, the hypertrophic chondrocytes also begin synthesis of bone-characteristic type I and III collagens and deposit apatite crystals in the matrix, thus transforming hypertrophic cartilage into a bone-like tissue. Finally, they undergo apoptosis. As a result, the tissue becomes amenable to invasion by bone and bone marrow precursor cells, which then proceed to remove the hypertrophic tissue and replace it with definitive bone tissue.

A large number of studies have been carried out during the last several years to identify and characterize the mechanisms regulating endochondral ossification. Interest in these mechanisms reflects the fact that defects in endochondral ossification are associated, and probably cause, congenital and acquired conditions of skeletogenesis (Jacenko et al., *J. Rheumatol.* 22:39–41 (1995)). Interestingly, several molecules have been shown to have a negative role in endochondral ossification and to limit the rates at which chondrocytes progress from the immature to the hypertrophic stage. These molecules include fibroblast growth factor-2 (FGF-2), fibroblast growth factor receptor-3 (FGF-R3), parathyroid-related protein (PTH-rP), and Indian hedgehog (IHH) (Coffin, et al., *Mol. Biol. Cell*, 6:1861–1873 (1995); Colvin et al., *Nature Genet.*, 12:390–397 (1996); Vortkamp et al., *Science*, 273:613–622 (1996)). However, very few positive factors have been identified to date, which would have the critical role of counteracting the negative factors and allow the endochondral process to advance and reach its conclusion.

Pathologies associated with bone growth include osteoarthritis. Osteoarthritis is a degenerative disease of the joints that causes progressive loss of articular tissue. The disease, for which presently no cure or effective treatment exists, affects over 10% of the population over 60 years of age. Osteoarthritis is probably initiated by a number of factors, including mechanical insults derived from life-long use of the joints. Once articular cartilage is damaged, the disease progresses and numerous changes occur in the cells and matrix. At sites most affected by the disease, the articular chondrocytes can reinitiate proliferation and begin to acquire abnormal phenotypic traits. These include synthesis of type I and III collagens, cell hypertrophy, type X collagen synthesis, alkaline phosphatase activity increased proteolytic activity and even matrix mineralization (Hamerman, *New Engl. J. Med.* 320, 1322–1330 (1989); Nerlich, et al., *Vichows Archiv. B. Cell Pathol.* 63, 249–255 (1993); von der Mark, K. et al., *Acta Orthop. Scand.* 266, 125–129 (1995)). At the same time, while synthesis of proteoglycans increases, net proteoglycan content decreases because of increased matrix degradation by metalloproteases and other degradative enzymes. There are also reports that the articular chondrocytes can display signs of cellular degeneration and apoptosis. Once the articular cells disappear and the matrix degenerates, the tissue is replaced by non-fimctional scar tissue or even bony tissue.

Thus, a need exists for effective therapeutic methods for the treatment of cartilage and bone pathologies, including bone growth related diseases such as osteoarthritis.

SUMMARY OF THE INVENTION

The present invention provides a method for treating a cartilage or bone pathology comprising administering a therapeutically effective amount of a retinoid receptor antagonist. According to one preferred embodiment, the retinoid receptor antagonist is an RAR receptor antagonist, and preferably an RARαβγ receptor antagonist.

The present invention further provides a method for treating a cartilage or bone pathology comprising antagonizing RARγ receptors associated with the pathology.

In a further embodiment, the present invention provides a method for ameliorating the symptoms associated with cartilage and bone pathologies comprising administering a therapeutically effective amount of a retinoid receptor antagonist.

The invention additionally provides a method for treating a cartilage or bone pathology comprising administering a therapeutically effective amount of a pharmaceutical composition comprising a retinoid receptor antagonist and a pharmaceutically acceptable carrier or excipient.

DETAILED DESCRIPTION OF THE INVENTION

The present invention provides a method of treating cartilage and bone pathologies, including bone growth related diseases, comprising the use of retinoid receptor antagonists. Bone growth related diseases include those involving pathological ossification such as osteoarthritis, multiple cartilaginous exostoses and osteoblastic tumors including osteoid osteoma, osteosarcoma and osteoma; and osteitis deformans (see generally, *Pathological Basis of Disease*, Robbins, et al. W. B. Saunders Co. (1979)). At the molecular level retinoids exert their biological effects through two families of nuclear receptors, retinoic acid receptors (RARs) and retinoid X receptors (RXRs), which belong to the superfamily of steroid/thyroidlvitamin D3 nuclear receptors.

RARs and RXRs are ligand-dependent transcription factors which regulate gene expression in at least two different ways: (a) they upregulate the expression of genes by binding to the RA-responsive elements (RAREs) present in their promoters or (b) they down-regulate the expression of genes by antagonizing the enhancer action of certain other transcription factors, such as AP1. The distinct isotypes of RARs ($\alpha$, $\beta$ and $\gamma$) and RXRs ($\alpha$, $\beta$ and $\gamma$) are encoded by six separate genes. Each RAR isotype is further expressed as several isoforms differing in their N-terminal A region, which are generated by alternative splicing and/or by differential usage of more than one promotor. RAR$\alpha$ is expressed as two main isoforms ($\alpha$1 and $\alpha$2). RAR$\beta$ as four isoforms ($\beta$1, $\beta$2, $\beta$3 and $\beta$4) and RAR$\gamma$ as two main isoforms ($\gamma$1 and $\gamma$2). RARs are believed to function exclusively in vivo as RAR-RXR heterodimers.

It has been found that hypertrophic chondrocytes present in long bone models in the developing limb express high levels of RAR, specifically RAR$\gamma$, and contain endogenous retinoids. As described in detail in the Examples, to determine the roles of RAR$\gamma$ and endogenous retinoids, beads filled with retinoid antagonist AGN 109 were placed in the vicinity of the developing long bone models at early stages of chick embryo development. The embryos were then reincubated in the presence of RAR$\gamma$ antagonist and the effects of antagonist treatment determined at various time points. It was found that chondrocyte maturation and long bone development are interrupted by antagonist treatment. In control limbs, the long bone models contained hypertrophic chondrocytes in their central portions (called the diaphysis) that synthesized type X collagen, alkaline phosphatase, and were mineralizing their matrix. Moreover, the hypertrophic cartilage was undergoing invasion by bone and marrow precursor cells and active bone deposition. In sharp contrast, the retinoid antagonist-treated long bones were entirely cartilaginous and contained no hypertrophic chondrocytes, type X collagen or alkaline phosphatase. In addition, calcium deposition and bone formation was not observed in the test group. Thus, retinoids are positive regulators of endochondral ossification, and appear to interfere with normal retinoid signaling by treatment with retinoid antagonists which blocks chondrocyte maturation and endochondral ossification (see also, Koyama et al., *Develop. Biol.* 208(2): 375–391 (1999)).

Accordingly, the present invention provides methods for interrupting or even reversing the acquisition of growth plate-like traits by articular chondrocytes during osteoarthritis or other conditions of articular cartilage leading to calcium deposition. Articular chondrocytes are those chondrocytes located in the skeletal joints. Thus, suitable retinoid receptor antagonists should prevent (a) hypertrophy of the cells, (b) expression of metalloproteases and alkaline phosphatase activity, (c) mineral deposition and even apoptosis, and (d) switches in collagen types, all of which occur in articular chondrocytes during the disease process. By preventing or slowing down such phenotypic changes, the antagonists should permit articular chondrocytes to carry out more effective repair of the matrix and tissue and may cause cessation of the degenerative process. The methods of the present invention are not linked to effecting articular chondrocytes but may be used to effect chondrocytes at any location in the skeletal system and associated with any phase of skeletal development or bone growth related pathology.

Any retinoid receptor antagonist presently known in the art, or subsequently developed, may be used in practicing the claimed methods. The synthesis of exemplary receptor antagonists is described, by way of example only, in U.S. Pat. Nos. 5,877,207; 5,514,825; 5,648,514; 5,728,846; 5,739,338; 5,760,276; 5,776,699; 5,773,594; 5,763,635; and 5,808,124 and U.S. Ser. Nos. 08/840,040 and 08/845,019, incorporated herein by reference in their entireties.

In a preferred method, the antagonist is an RAR antagonist, and more preferably an RAR$\alpha\beta\gamma$ antagonist. However, antagonists with activity specific for a particular isotype and/or isoform or a combination thereof may also be used in the present methods. Thus, antagonists specific for RAR$\alpha$, $\beta$, $\gamma$ or combinations thereof, such as $\alpha\beta$, $\alpha\gamma$ and $\beta\gamma$ may be used. Such receptor isotype specific antagonists may be preferred in order to reduce any side effects associated with the use of non-specific antagonists.

As used herein, "agonist" means a compound that will stimulate the ligand-mediated transactivational activity of the specified retinoid receptor.

As used herein, "antagonist" means a compound that will inhibit or block the ligand-mediated transactivational activity of the specified retinoid receptor.

As used herein, "inverse agonist" means a compound that will decrease a basal level of transactivational activity of the specified retinoid receptor, wherein the basal level is that amount of transactivational activity observed in the absence of added agonist.

As used herein, the term "selective" means that a given ligand demonstrates at least about a 10 fold greater binding affinity, as indicated by, for example, $K_d$ value, (dissociation constant) for one receptor subtype than for another receptor subtype.

As used herein, the term "specific" means that a given ligand demonstrates at least about a 500 fold greater binding affinity, and more preferably at least about a 1000 fold greater binding affinity, for one receptor subtype than for another receptor subtype.

As used herein, the term "treating" means reducing or slowing the progression of a disease. Alternatively, or additionally, the term means to remedy or cure a disease. Where the disease is tumor related, the term treating means to inhibit cancer cell growth and/or reduce the sign of a tumor.

The term "ameliorating" means reducing the symptoms associated with a particular disease, such as pain and inflammation.

In a preferred method of treatment, the antagonist is a compound of formula (I)

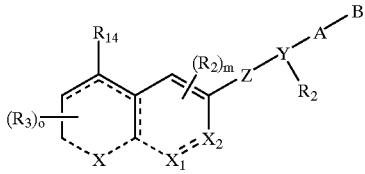

(I)

wherein

X is S, SO, $SO_2$, O, $NR_1$, $[C(R_1)_2]_n$ where each $R_1$ is independently or together H or alkyl of 1 to 6 carbons, and n is 1 or 2;

or X is absent;

$X_1$ and $X_2$ are each C; or $X_1$ is absent and $X_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

provided that at least X is present, or $X_1$ and $X_2$ are each C;

- - - are optionally present bonds;

each $R_2$ is independently or together hydrogen, lower alkyl of 1 to 6 carbons, F, Cl, Br, I, $CF_3$, fluoro substituted alkyl of 1 to 6 carbons, OH, SH, alkoxy of 1 to 6 carbons, alkylthio of 1 to 6 carbons, $NH_2$, $NR_1H$, $N(R_1)_2$, $N(R_1)COR_1$, $NR_1CON(R_1)_2$ or $OCOR_1$;

each $R_3$ is independently or together hydrogen, lower alkyl of 1 to 6 carbons, F, Cl, Br or I;

m is an integer having a value of 0–3;

o is an integer having a value of 0–3;

Z is —C≡C—, —N=N—, —N=$CR_1$—, —$CR_1$=N—, —($CR_1$=$CR_1$)$_{n'}$— where n' is an integer having the value 0–5, —CO—$NR_1$—, —CS—$NR_1$—, —NR1—CO—, —$NR_1$CS—, —COO—, —OCO—, CSO— or —OCS—;

Y is a phenyl or naphthyl group, or heteroaryl selected from the group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is —($CR_1$=$CR_1$)$_{n'}$— and n' is 3, 4 or 5 then Y represents a direct valence bond between said —($CR_1$=$CR_1$)$_{n'}$ group and B;

A is $(CH_2)_q$ where q is 1–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds; or is a direct bond or is absent;

B is hydrogen, COOH, $COOR_8$, $CONR_9R_{10}$, $CH_2OH$, $CH_2OR_{11}$, $CH_2OCOR_{11}$, CHO, $CH(OR_{12})_2$, $CHOR_{13}O$, $COR_7$, $CR_7(OR_{12})_2$, $CR_7OR_{13}O$, or tri-low alkylsilyl, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons; and $R_{14}$ is $(R_{15})_r$-phenyl, $(R_{15})_r$-naphthyl, or $(R_{15})_r$-heteroaryl where the heteroaryl group has 1 to 3 heteroatoms selected from the group consisting of O, S and N; r is an integer having a value of 0–6; and $R_{15}$ is independently H, F, Cl, Br, I, $NO_2$, $N(R_8)_2$, $N(R_8)COR_8$, $NR_8CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or (trialkylsilyl)oxy group where the alkyl groups independently have 1 to 6 carbons; or a pharmaceutically acceptable salt or ester thereof.

According to one embodiment, X is present and $X_1$ is absent, providing compounds of formula (Ia):

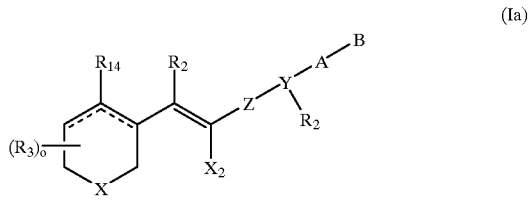

(Ia)

In another embodiment, X is absent and $X_1$ and $X_2$ are C, providing compounds of formula (Ib):

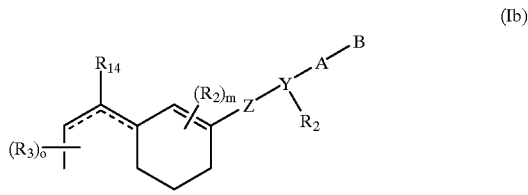

(Ib)

In yet a further particularly preferred embodiment, X is present and $X_1$ and $X_2$ are C, providing compounds of formula (Ic):

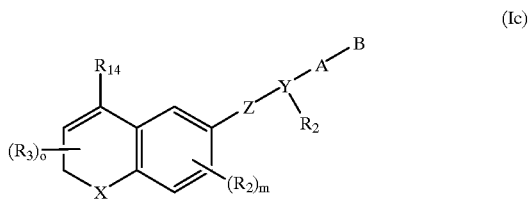

(Ic)

In preferred embodiments of formulas I, Ia, Ib and Ic, Y is phenyl and $R_{14}$ is $(R_{15})_r$-phenyl, where preferably the bond between $R_{14}$ and the heterocyclic moiety comprising X allows for free rotation of the $R_{14}$ group. In a further embodiment, —Y($R_2$)—A—B is —phenyl—COOH.

Specific antagonists within the scope of formula (I), method of synthesis as well as definitions of terminology used to define compounds of formula (I), are more fully described in U.S. Pat. No. 5,776,699. Further examples of compounds which may be used in practicing the present invention include compounds of formulas (II) through (V):

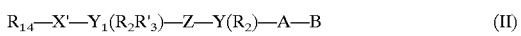

(II)

where

X' is O, S, SO, $SO_2$, N, $NR_3$ or $C(R_3)_2$; or —X'—$R_{14}$ is —$C(R_{14})H_2$ or —$C(R_{14})$—$(CH_2)_n$H where n is 1–6;

$Y_1$ is phenyl, naphthyl or heteroaryl selected from the group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being optionally substituted with one $R'_3$ and one or two $R_2$ groups;

$R'_3$ is H, ($C_1$–$C_{10}$) alkyl, 1-adamantyl, 2-tetrahydropyranoxy, trialkylsilanyl and trialkylsilanyloxy where alkyl comprises 1 to 6 carbons, alkoxy and alkylthio where alkyl comprises 1 to 10 carbons, or $OCH_2O(C_{1-6})$alkyl; and Z, Y, A, B, $R_2$, $R_3$ and $R_{14}$ are as defined above; where preferred embodiments include compounds of formula (IIa):

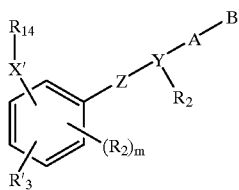

(IIa)

where m is 0–2; where further preferred embodiments include compounds of formula (IIb):

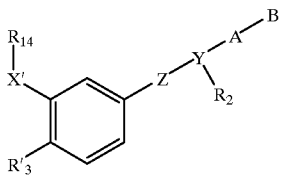

(IIb)

where preferably $R'_3$ is alkyl; and where additional embodiments include compounds of formula (IIc):

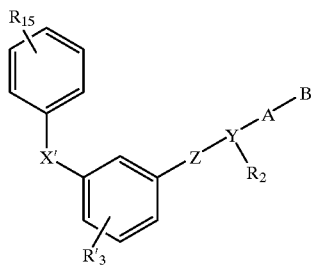

(IIc)

compounds of formula (III):

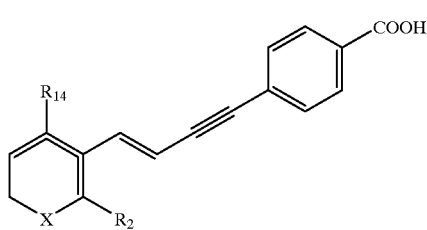

(III)

where $R_2$ is as described above and additionally preferably $C_1$–$C_6$ alkenyl, and X and $R_{14}$ are as described above;

compounds of formula (IV):

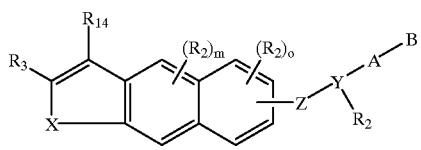

(IV)

wherein X is S, SO, $SO_2$, O, $NR_1$, $[C(R_1)_2]_n$, —$C(R_1)_2$—$NR_1$—, —$C(R_1)_2$—S—, —$C(R_1)_2$—O— or —$C(R_1)_2$—$(R_1)_2$—, where $R_1$, $R_2$, $R_3$, $R_{14}$, Z, Y, A, B, m and o are as described above; where preferred embodiments include compounds of formula (IVa):

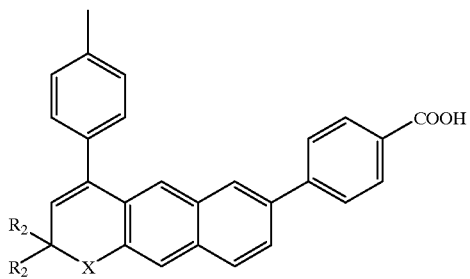

(IVa)

and compounds of formula (V):

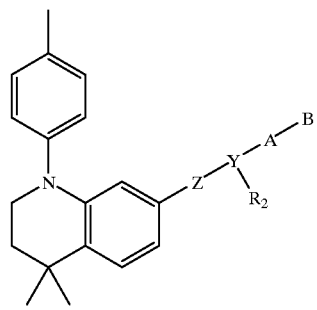

(V)

where Z, Y, A, B and $R_2$ are as described above.

Another preferred class of compounds are those of formula (VI):

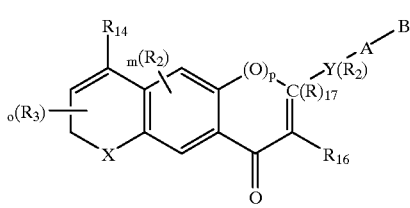

(VI)

wherein
X, $R_2$, $R_3$, m, o, Y, A, B, $R_{14}$ and $R_{15}$ are as defined above, and;
$R_{16}$ is H or lower alkyl of 1 to 6 carbons;
$R_{17}$ is H, lower alkyl of 1 to 6 carbons, OH or $OCOR_{11}$, where $R_{11}$ is defined above, or $R_{17}$ is absent; and
p is 0 or 1, with the proviso that when p is 1 then $R_{17}$ is absent.

A further preferred class of compounds are those of formula (VII):

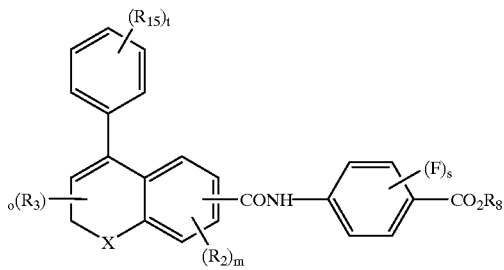

where

X, $R_1$ $R_2$ m, $R_3$ and o are as defined above;

s is an integer having a value of 1–3; and $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl;

$R_{15}$ is as defined above;

t is an integer having a value of 0–5, where the CONH group is in the 6 or 7 position of the benzopyran, and in the 2 or 3 position of the dihydronaphthaline ring; or a pharmaceutically acceptable salt thereof.

Another preferred class are compounds of formula (VIII):

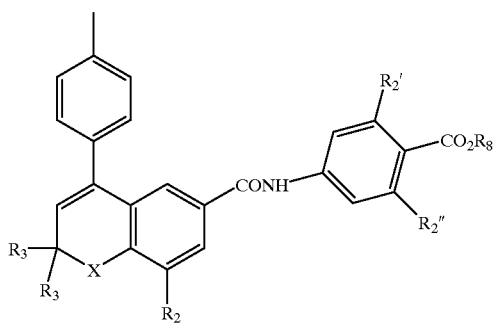

where

X is preferably $C(CH_3)_2$ or O;

$R_2$ is preferably H or Br;

$R_{2'}$ and $R_{2''}$ independently are H or F;

$R_3$ is preferably H or $CH_3$; and $R_8$ is preferably H, lower alkyl of 1 to 6 carbons; or a pharmaceutically acceptable salt thereof.

A further preferred class of such compounds are of formula (IX):

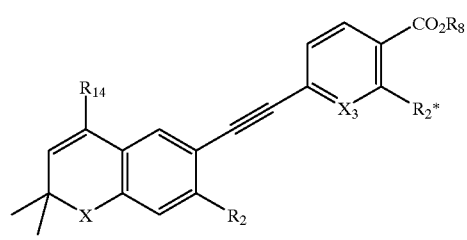

where $X_1$ is preferably S or O;

$X_3$ is CH or N;

$R_2$ is preferably H, F, $CF_3$ or alkoxy of 1 to 6 carbons;

$R_2^*$ is H, F or $CF_3$;

$R_8$ is preferably H, or lower alkyl of 1 to 6 carbons; and $R_{14}$ is preferably unsubstituted phenyl, thienyl or pyridyl, or phenyl, thienyl or pyridyl substituted with one to three $R_{15}$ groups, where $R_{15}$ is preferably lower alkyl of 1 to 6 carbons, chlorine, $CF_3$, or alkoxy of 1 to 6 carbons, or a pharmaceutically acceptable salt thereof.

In a preferred embodiment of compounds of formula (IX), X is S, $R_2$ is H, F or $OCH_3$; $R_2^*$ is H or F; $R_8$ is H, or lower alkyl of 1 to 6 carbons; and $R_{14}$ is selected from the group consisting of phenyl, 4-(lower-alkyl)phenyl, 5-(lower alkyl)-2-thienyl, and 6-(lower alkyl)-3-pyridyl where lower alkyl has 1 to 6 carbons; or a pharmaceutically acceptable salt thereof. In one particular embodiment, $R_2$ is H; $R_2^*$ is H; $X_3$ is CH; and $R_{14}$ is ethyl.

In another preferred embodiment of compounds of formula (IX), X is O; $R_2$ is H; $R_2^*$ is H or F; $R_8$ is H or lower alkyl of 1 to 6 carbons; and $R_{14}$ is selected from the group consisting of phenyl, and 4-(lower-alkyl)phenyl, where lower alkyl has 1 to 6 carbons, or a pharmaceutically acceptable salt thereof.

Yet another preferred group of compounds is of formula (X):

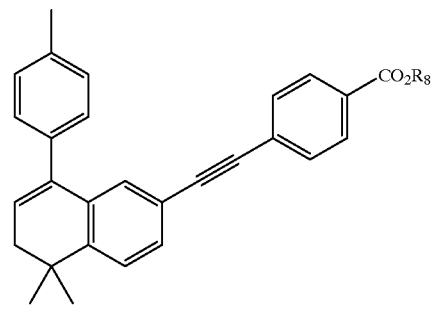

where $R_8$ is H, lower alkyl of 1 to 6 carbons, or a pharmaceutically acceptable salt of said compound. When $R_8$ is H, this compound is AGN 109, a preferred embodiment.

Furthermore, the structures of additional compounds useful in the present invention are disclosed below.

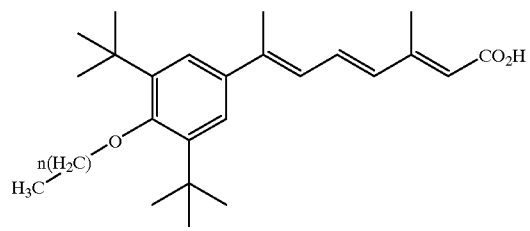

where n is an integer from 1 to 10.

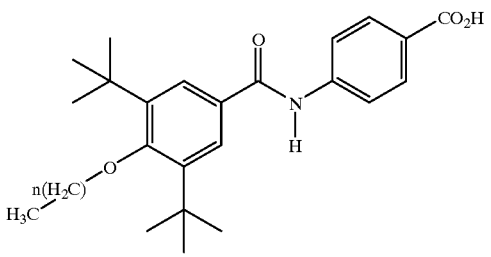

where n is an integer from 1 to 10.

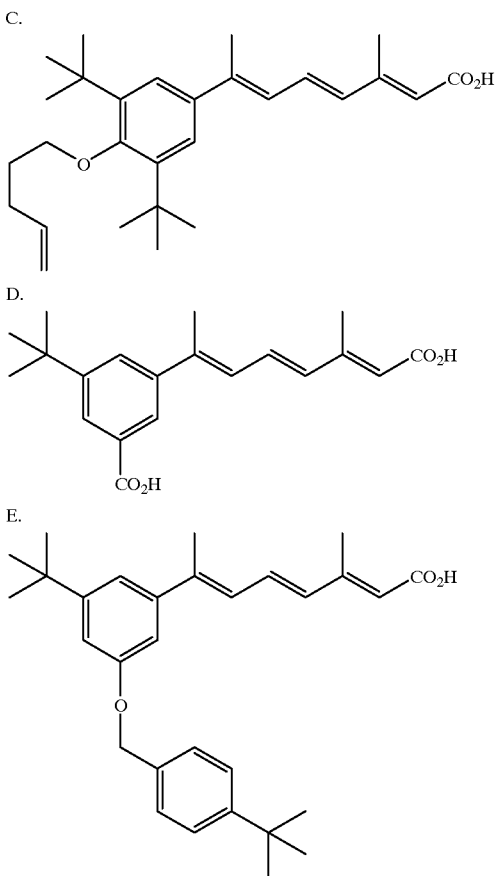

As discussed above, any compound or agent having retinoid receptor antagonist activity may be used. Means for determining antagonist activity of a given agent or compound are known in the art. For example, a holoreceptor transactivation assay and a ligand binding assay which measure the antagonist/agonist like activity of the compounds of the invention, or their ability to bind to the several retinoid receptor subtypes, respectively, are described in published PCT Application No. WO 93/11755 (particularly on pages 30–33 and 37–41) published on Jun. 24, 1993, the specification of which is also incorporated herein by reference.

A pharmaceutically acceptable salt may be prepared for any compound in this invention having a functionality capable of forming a salt, for example, an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. In such cases, preferred salts are those formed with inorganic acids such as hydrochloric acid, sulfuric acid or phosphoric acid. Any of a number of simple organic acids such as mono-, di- or tri-acid may also be used.

Some of the compounds of the present invention may have trans and cis (E and Z) isomers. In addition, the compounds of the present invention may contain one or more chiral centers and therefore may exist in enantiomeric and diastereomeric forms. Still further oxime and related compounds of the present invention may exist in syn and anti isomeric forms. The scope of the present invention is intended to cover all such isomers per se, as well as mixtures of cis and trans isomers, mixtures of syn and anti isomers, mixtures of diastereomers and racemic mixtures of enantiomers (optical isomers) as well. In the present application when no specific mention is made of the configuration (cis, trans, syn or anti or R or S) of a compound (or of an asymmetric carbon) then a mixture of such isomers, or either one of the isomers is intended. In a similar vein, when in the chemical structural formulas of this application a straight line representing a valence bond is drawn to an asymmetric carbon, then isomers of both R and S configuration, as well as their mixtures are intended. Defined stereochemistry about an asymmetric carbon is indicated in the formulas (where applicable) by a solid triangle showing β-configuration, or by a hashed line showing α-configuration.

The present invention also provides pharmaceutical compositions comprising one or more compounds of the invention together with a pharmaceutically acceptable diluent or excipient. Preferably such compositions are in unit dosage forms such as tablets, pills, capsules (including sustained-release or delayed-release formulations), powders, granules, elixirs, tinctures, syrups and emulsions, sterile parenteral solutions or suspensions, aerosol or liquid sprays, drops, ampoules, auto-injector devices or suppositories; for oral, parenteral (e.g., intravenous, intramuscular or subcutaneous), intranasal, sublingual or rectal administration, or for administration by inhalation or insufflation, and may be formulated in an appropriate manner and in accordance with accepted practices such as those disclosed in *Remington's Pharmaceutical Sciences*, Gennaro, Ed., Mack Publishing Co., Easton Pa., 1990. Alternatively, the compositions may be in sustained-release form suitable, for example, for once-weekly or once-monthly administration; for example, an insoluble salt of the active compound, such as the decanoate salt, may be adapted to provide a depot preparation for intramuscular injection. The present invention also contemplates providing suitable topical formulations for administration to, e.g. eye or skin or mucosa.

For instance, for oral administration in the form of a tablet or capsule, the active drug component can be combined with an oral, non-toxic pharmaceutically acceptable inert carrier such as ethanol, pharmaceutically acceptable oils, glycerol, water and the like. Moreover, when desired or necessary, suitable binders, lubricants, disintegrating agents, flavoring agents and coloring agents can also be incorporated into the mixture. Suitable binders include, without limitation, starch, gelatin, natural sugars such as glucose or beta-lactose, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For preparing solid compositions such as tablets, the active ingredient may be mixed with a suitable pharmaceutical excipient, e.g., such as the ones described above, and other pharmaceutical diluents, e.g., water, to form a solid preformulation composition containing a homogeneous mixture of a compound of the present invention, or a pharmaceutically acceptable salt thereof. By the term "homogeneous" is meant that the active ingredient is dispersed evenly throughout the composition so that the composition may be readily subdivided into equally effective unit dosage forms such as tablets, pills and capsules. The solid preformulation composition may then be subdivided into unit dosage forms of the type described above containing from 0.1 to about 50 mg of the active ingredient of the present invention.

In another embodiment, the tablets or pills of the present composition may be coated or otherwise compounded to provide a dosage form affording the advantage of prolonged action. For example, the tablet or pill can comprise an inner core containing the active compound and an outer layer as a coating surrounding the core. The outer coating may be an enteric layer which serves to resist disintegration in the stomach and permits the inner core to pass intact into the duodenum or to be delayed in release. A variety of materials can be used for such enteric layers or coatings, such materials including a number of polymeric acids and mixtures of polymeric acids with conventional materials such as shellac, cetyl alcohol and cellulose acetate.

The liquid forms in which the present compositions may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical carriers. Suitable dispersing or suspending agents for aqueous suspensions include synthetic and natural gums such as tragacanth, acacia, alginate, dextran, sodium carboxymethylcellulose, gelatin, methylcellulose or polyvinyl-pyrrolidone. Other dispersing agents which may be employed include glycerin and the like. For parenteral administration, sterile suspensions and solutions are desired. Isotonic preparations which generally contain suitable preservatives are employed when intravenous administration is desired. The compositions can also be formulated as an ophthalmic solution or suspension formation, i.e., eye drops, for ocular administration.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

Advantageously, compounds of the present invention may be administered in a single daily dose, or the total daily dosage may be administered in divided doses two, three or four times daily. Furthermore, compounds for the present invention may be administered in intranasal form via topical use of suitable intranasal vehicles, or via transdermal routes, using those forms of transdermal skin patches well known to persons skilled in the art. To be administered in the form of a transdermal delivery system, the Adosage administration will, of course, be continuous rather than intermittent throughout the dosage regimen, and dosage levels will require that this be taken into consideration when formulated.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound employed. A physician or veterinarian of ordinary skill can readily determine and prescribe the effective amount of the drug required to prevent, counter or arrest the progress of the disease or disorder which is being treated.

The daily dosage of retinoid receptor antagonists or reverse agonists may vary over a wide range from 0.01 to 100 mg per adult human per day. For oral administration, the compositions are preferably provided in the form of tablets containing 0.01, 0.05, 0.1, 0.5, 1.0, 2.5, 5.0, 10.0, 15.0, 25.0 or 50.0 mg of the active ingredient for the symptomatic adjustment of the dosage to the patient to be treated. A unit dose typically contains from about 0.001 mg to about 50 mg of the active ingredient, preferably from about 1 mg to about 10 mg of active ingredient. An effective amount of the drug is ordinarily supplied at a dosage level of from about 0.0001 mg/kg to about 25 mg/kg of body weight per day. Preferably, the range is from about 0.001 to 10 mg/kg of body weight per day, and especially from about 0.001 mg/kg to 1 mg/kg of body weight per day. The compounds may be administered on a regimen of 1 to 4 times per day.

All references cited are incorporated herein by reference in their entireties.

The invention is disclosed in further detail in the following examples, which are not in any way intended to limit the scope of the invention as claimed.

EXAMPLES

Example I

Materials and Methods

In situ Hybridization

This procedure was carried out as described previously (Noji et al., *Acta Histochem. Cytochem.* 23, 353–366 (1990); Koyama et al., *Dev. Dynam.* 203, 152–162 (1995)). Briefly, chick embryos or embryo parts were fixed with 4% paraformaldehyde for 4 hr or overnight, embedded in paraffin and sectioned. The 5 μm thick sections were pretreated with 1 μg/ml proteinase K (Sigma, St. Louis, Mo.) in 50 mM Tris, 5 mM EDTA, pH 7.5 at room temperature for 1 min, immediately postfixed in 4% paraformaldehyde buffer for 10 min, and then washed twice in PBS containing 2 mg/ml glycine for 10 min/wash. Sections were treated for 15 min with a freshly prepared solution of 0.25% acetic anhydride in triethanolamine buffer. Sections were hybridized with $^{35}$S-labeled antisense or sense chick cDNA riboprobes (approximately $1 \times 10^6$ DPM/section) at 50° C. for 16 hr. After hybridization, slides were washed three times with 2×SSC containing 50% formamide at 50° C. for 20 min/ wash, treated with 20 μg/ml RNaseA for 30 min at 37° C., and finally washed three times with 0.1×SSC at 50° C. for 10 min/wash. Sections were coated with Kodak NTB3 emulsion diluted 1:1 with water, exposed for 7 days, and developed with Kodak D19 for 3 min at 20° C. After staining with hematoxylin and eosin, slides were analyzed with a Nikon microscope using bright and dark field optics.

The chick cDNA probes used were: the 1.6 kb RARα and 0.9 kb RARβ clones encompassing the ligand binding domain (Noji et al., Nature 350, 83–86 (1991)); a 0.16 kb RARγ subdlone (nucleotides 444–607) prepared from full length RARγ2 (Michaille et al., Dev. Dynam. 201, 334–343 (1994)) and encoding a portion of domain C; a 0.56 kb Ihh clone encoding part of the N-terninal domain (Vortkamp et al., Science 273, 613–633 (1996)); the type I collagen pGEM821, a 0.821 kb clone from the 3' end of type I collagen subunit α12(I) (Bennett et al., J. Biol. Chem. 264, 8402–8409 (1989)); the type II collagen clone pDLr2 (Leboy et al., J. Biol. Chem. 264, 17281–17286 (1989)), a 0.8 kb clone from the 3' region of type II collagen (Young et al., Nucl. Acids Res. 12, 4207–4228 (1984)); the 0.197 kb type X collagen clone pDLr10 (Leboy et al., J. Biol. Chem. 264, 17281–17286 (1989)); and the 1.1 kb clone pMMPP2 containing the full coding sequence of osteopontin (Moore et al., Biochemistry 30, 2501–2508 (1991)).

Antagonist Treatment

The RAR antagonists used were AGN 109 (Allergan Pharmaceuticals, Irvine, Calif.) and Ro 41–5253 (shown below) (Hoffnann-LaRoche, Basel, Switzerland).

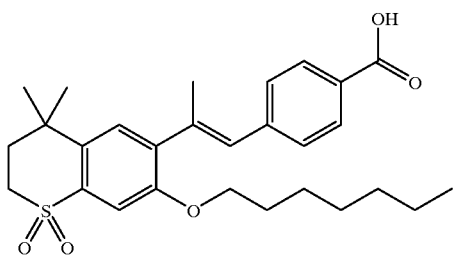

Ro 41–5253 exerts antagonistic effects on all RAR isoforms but preferentially on RARα ($IC_{50}$=60 nM); its $IC_{50}$ for RARγ is 3300 nM (Apfel et al., Proc. Natl. Acad. Sci. USA 89, 7129–7133 (1992); Keidel et al., Mol. Cell. Biol. 14, 287–298 (1994)). AGN 109 inhibits equally well RARα, β and γ, and has a nearly 500-fold lower $IC_{50}$ for RARγ (5+1 nM) (Klein et al., J. Biol. Chem. 271, 22692–22696 (1996)) compared to Ro 41–5253. AG1-X2 ion-exchange beads of 200–400 μm in diameter were soaked for 1 hr in solutions of Ro 41–5253 or AGN 109 at concentrations ranging from 3.5 μM to 3.5 mM. This range of concentrations was based on previous studies (see, for example, Lu et al., Development 124, 1643–1651 (1997)). Antagonist solutions were prepared in DMSO and used under yellow light conditions; control beads were soaked in DMSO alone. Beads were then dipped very briefly in phenol red-containing saline (HBSS) so that they were more readily visible during implantation.

Antagonist-containing or control beads were implanted in the wing bud of stage 21–22 (Day 3–3.5) or stage 27–28 (Day 5.5) chick embryos (Hamburger and Hamilton, J. Morphol. 88, 49–92 (1951)); contralateral wing bud served as control. A small window was opened in the egg shell and a small incision was made on the antero-dorsal proximal portion of the bud. One bead or several beads were then placed in the vicinity of the prospective humerus as specified below, and eggs were sealed and returned to the incubator.

On the day of analysis, embryos were sacrificed by decapitation, and control and operated wings were examined by microscopy, using a Nikon SMZ-U dissecting photornicroscope, and humerus length was measured micrometrically. Because length of control humeri varied slightly from embryo to embryo, possibly reflecting slight differences in age, humeri were considered affected by antagonist treatment only if their length was shortened at least 25% over control value. Companion control and antagonist-treated limbs were processed for histology and in situ hybridization using tissue sections.

Chondrocyte Cultures

Cell populations rich in prehypertrophic and early hypertrophic chondrocytes were isolated from the cephalic core region of Day 17–18 chick embryo sterna, while immature chondrocytes were isolated from the caudal sternal region (Gibson and Flint, J. Cell Biol. 101, 277–284 (1985); Pacifici et al., Exp. Cell Res. 195, 3846 (1991); Iwamoto et al., Exp. Cell Res. 207, 413420 (1993b)). The dissected cephalic and caudal tissues were incubated for 1 hr at 37° C. in saline containing 0.1% type 1-S collagenase (Sigma Chemical Co., St. Louis, Mo.); the cells released after this incubation were discarded as they consisted mainly of perichondrial and blood cells. The remaining tissue was incubated in a fresh mixture of 0.25% trypsin and 0.1% collagenase for 3 hr at which point it was completely digested. The freshly isolated chondrocytes were plated at a density of $2 \times 10^5$ cells/well in 12-well plates, $1 \times 10^6$ cells/60 mm dish or $3 \times 10^6$ cells/100 mm dish. The cephalic core chondrocytes were grown continuously, without subculturing, for 2 to 3 weeks in monolayer. During the first 2 days, cultures received 4 U/ml of testicular hyaluronidase to minimize cell detachment (Leboy et al., J. Biol. Chem. 264, 17281–17286 (1989)), and cultures became confluent by 2 weeks. The caudal immature chondrocytes were first grown for 5 days at which point floating immature chondrocytes were separated from attached contaminating fibroblastic cells. The floating cells were trypsinized and replated in secondary cultures in the presence of hyaluronidase to increase cell attachment. Cultures were fed every other day with Dulbecco's modified high-glucose Eagle's medium (GIBCO BRL, Gaithersburg, Md.) containing 10% defined fetal calf serum (Hyclone, Logan, Utah), 2 mM L-glutamine, and 50 U/ml penicillin and streptomycin (Pacifici et al., Exp. Cell Res. 195, 38–46 (1991)). When indicated, cultures were treated with all-trans-RA (Sigmna) or combinations of all-trans-RA and Ro 41–5253. Stock solutions of these retinoids were prepared in DMSO and were diluted into working solutions in 95% ethanol; control dishes received an equivalent amount of vehicle without retinoids. To analyze mineralization, cephalic sternal control and retinoid-treated cultures were supplemented with 3 mM β-glycerophosphate to serve as a phosphate source. During these various regimens, medium was changed daily. To localize calcium deposits, the cell layers were stained with 0.5% alizarin red S solution, pH 4.0, for 5 min at room temperature. In experiments in which cultures were treated for 2, 4 or 6 days, retinoid treatments were initiated so that all cultures (including control cultures) were harvested simultaneously.

RNA Isolation and Analysis

Whole cellular RNA isolated from chick embryo cartilages and cultured chondrocytes by the guanidine isothiocynate method (Chomczynski and Sacchi, Anal. Biochem. 162, 156–159 (1987)) was denatured by glyoxalation, electrophoresed on 1% agarose gels at 10 or 30 μg/lane, and transferred to Hybond-N membranes by capillary blotting, as described previously (Oettinger and Pacifici, Exp. Cell Res. 191, 292–298 (1990); Iwamoto et al., *Exp. Cell Res.* 205, 213–224 (1993a)). Blots were stained with 0.04% methylene blue to verify that each sample had been transferred efficiently. Blots were hybridized for 16 hr to $^{32}$P-labeled riboprobes at a concentration of 2.5×10$^6$ DPM/ml of hybridization solution containing 50% formamide, 1.5× SSPE, 500 µg/ml sheared denatured salmon sperm DNA, 100 µg/ml tRNA, 0.5% (w/v) dry milk, and 1% SDS. The cDNA probes used were the same as those used for in situ hybridization. Hybridization temperature was 55° C. for RARγ and APase, and 60° C. for type X collagen. After hybridization, blots were rinsed several times at room temperature with 2×SSC and 0.5% SDS; a final high stringency rinse was with 0.1×SSC and 0.5% SDS at 70° C. Blots were exposed to Kodak BioMax x-ray films at −70° C.

Retinoid Analysis

Semi-quantitative analysis of endogenous retinoid levels in embryonic tissues was carried out using a sensitive in vitro reporter assay (Wagner et al., *Development* 116, 55–66 (1992); McCaffery et al., *Development* 115, 371–382 (1992)). The β-gal assay consists of an F9 teratocarcinoma cell line stably transfected with a reporter construct which contains a 64 bp retinoic acid-response element (RARE) from the promoter region of the human RARβ gene (Ellis et al., *Nature* 343–377–181 (1990)) placed immediately upstream of the *E. coli* lacZ gene. The F9 cell line constitutively expresses RARα, β and γ(Zelent et al., *Nature* 339, 714–717 (1989)), which confer retinoid responsivity to the stably transfected construct. Cells were maintained on gelatin-coated dishes in modified L15 CO$_2$ tissue culture medium (Specialty Media, Lavallette, N.J.) supplemented with 20% fetal calf serum and 0.8 mg/ml G418 (complete medium), and were used when 80–90% confluent. In this culture condition, the reporter cells have been shown to be very sensitive (i.e., high expression of β-gal) to exogenous all-trans-RA treatment at concentrations as low as 0.01 nM (Wagner et al., *Development* 116, 55–66 (1992)). In these cells exogenous 9-cis-RA, a ligand for both RXR$_s$ and RARs (Levin et al., *Nature* 355, 359–361 (1992)), stimulates transcription with a 10-fold lower efficiency than in response to all-trans-RA treatment (unpublished observations).

To prepare tissue extracts, tissues were surgically isolated from Day 10 chick embryos and included. The metaphyseal-diaphyseal portion of cartilaginous humerus and tibia from which adherent perichondral tissues were carefully removed, liver, brain, gizzard and heart. During isolation, all tissues were kept in saline on ice under yellow safety light conditions to protect the retinoids. About 200 mg of each tissue or organ were then homogenized with a Polytron in 0.9 ml of L15 complete medium at 4° C. and samples were then quick-frozen in dry ice for complete cell disruption. Samples were thawed in iced water and were incubated at 4° C. for 1 hr to extract retinoids. Extracts were centrifuged at 13,000 g for 15 min at 4° C. The resulting supernatants were carefully separated from the pellet and directly added to semiconfluent cultures of F9 reporter cells grown in 22 mm multiwell plates (0.4 ml/well). Cultures were reincubated for 24 hr and were then processed for histochemical detection of β-galactosidase activity (Lim and Chae, *Biotechniques* 7, 576, 579 (1989)).

To confirm that β-galactosidase activity was proportional to retinoid concentration, parallel cultures of semiconfluent F9 cell cultures were treated with known amounts of all-trans-RA ranging from 1 M to 2 µM (from 100 X stock solutions in 95% ethanol), incubated for 24 hrs and then processed for quantitative analysis of β-galactosidase activity. Briefly, cultures were fixed with 0.1% glutaraldehyde in 0.1 M phosphate buffer pH 7.0 for 15 min at room temperature. After rinsing with PBS, cultures were stained with a solution of 0.2% X-Gal in phosphate buffer for 16 hrs at 37° C. After rinsing again, cultures were extracted with 0.2 ml of DMSO and absorbance of the extracted material was determined at 655 nm using a Perkin-Elmer spectrophotometer. Under these conditions, the F9 cells exhibited a linear increase in β-galactosidase activity between 1 nM to 0.5 µM all-trans-RA.

Example II

Results

RAR Gene Expression During Skeletogenesis

In a first set of experiments (see Example I, In situ Hybridization), the expression patterns of RARα, β and γ were determined at different stages of chick limb skeletogenesis. Longitudinal serial sections of limb skeletal elements were processed for in situ hybridization using $^{35}$S-labeled antisense riboprobes encoding antisense chick RARα, β or γ; as controls, sections were hybridized with radiolabeled sense probes targeted to these RAR's. When early newly-emerged skeletal elements were examined, such as the stage 27–28 (Day 5.5) chick embryo humerus which contains only immature chondrocytes and does not yet display growth plates, it was found that the gene expression levels of RARα and γ were low and diffuse, the level of hybridization signal within the newly-formed cartilaginous tissue was somewhat lower than that detectable in the surrounding mesenchymal and connective tissues. In contrast to the diffuse nondescript patterns of RARα and γ, gene expression of RARβ was distinct and quite pronounced in the perichondrial tissue, particularly along the incipient diaphysis, though it was very low in the cartilaginous tissue itself. Hybridization with sense RAR probes yielded barely detectable signal. The overall cartilaginous tissue was delineated by hybridization with a type II collagen antisense probe.

Between Days 8 and 10 of limb development, the long bone cartilaginous models acquire more definitive morphological characteristics and organization. They displayed prospective articular chondrocytes (ac) at their epiphyseal ends and long growth plates with well defined proliferative (pz), postproliferative-prehypertrophic (phz) and hypertrophic (hz) zones occupying the metaphysis and diaphysis. In addition, the 15 diaphysis begins the process of endochondral ossification and is surrounded by an intramembranous bony collar (Fell, *J. Morphol. Physiol.* 40, 417–459 (1925); Scott-Savage and Hall, *J. Morphol* 162, 453–464 (1979); Osdoby and Caplan, *Dev. Biol.* 86, 147–156 (1981); Koyama et al., *Dev. Dynam.* 203, 152–162 (1995)). In situ hybridization on serial sections of Day 10 chick embryo wing showed that while RARα gene expression remained low and diffuse throughout the cartilaginous tissue and RARβ expression was still strong in perichondrium, RARγ expression was markedly up-regulated in the hypertrophic zone of growth plate. Hybridization with a probe encoding type X collagen, a marker of hypertrophic chondrocytes (Gibson and Flint, *J. Cell Biol.* 101, 277–284 (1985)), confirmed that there was a significant similarity between the topographical distribution of type X collagen transcripts and RARγ transcripts, though the increase in RARγ transcripts slightly preceded that in type X collagen transcripts. Analysis of other markers revealed that the RARγ- and type X collagen-rich chondrocytes were preceded in the growth plate by prehypertrophic chondrocytes expressing the morphogenetic factor Indian hedgehog (Ihh) (Koyama et al., *Dev. Dynam.* 207, 344–354 (1996a); Vortkamp et al., *Sci-* ence 273, 613–622 (1996)), and were followed by mineralizing post-hypertrophic chondrocytes undergoing endochondral ossification and expressing late maturation markers such as osteopontin (Iwamoto et al., *Exp. Cell Res.* 207, 413420 (1993b)). Osteopontin expression was also detectable in the developing bony collar surrounding the diaphysis and metaphysis. As expected, type II collagen gene expression was strong throughout most of the cartilaginous tissue but was markedly down-regulated in the mineralizing and endochondral ossification zones, while type I collagen RNA was confined to the bony collar, perichondrial tissue and other surrounding connective tissues. Similar results were obtained with Day 8.5 (stage 35) embryos (see below).

The relationship between increased RARβ expression and emergence of hypertrophic chondrocytes was further analyzed in the digit area of Day 10 limbs, which contains short skeletal elements at different stages of development along the proximal-to-dital axis in close proximity to each other. Indeed, it was found that the developmentally older proximal phalangeal (pp) elements contained abundant RARγ transcripts and numerous hypertrophic chondrocytes in the diaphysis, whereas the developmentally younger medial phalange (mp) contained fewer hypertrophic cells and lower amounts of RARγ transcripts and the even younger distal phalange (dp) contained neither. Closer inspection of the diaphyseal region of the proximal phalange revealed that whereas the RARγ transcripts were present throughout the diaphysis, the hypertrophic chondrocytes were not. These cells were much more obvious and numerous at the periphery of the diaphysis than its center.

Taken together, the above data indicate that the RARβ display differential patterns of gene expression during limb chondrocyte maturation and skeletogenesis. In particular, while RARα expression remains broad and diffuse, RARγ expression is selectively up-regulated just before the chondrocytes become fully hypertrophic and remains high in the hypertrophic cells. The data also indicate that the first hypertrophic chondrocytes form at the periphery of cartilaginous elements.

Retinoid Bioassays

It was determined next whether the cartilaginous skeletal elements present in limbs at later stages of development also contain endogenous retinoids (see Example I, Retinoid Analysis). If so, the retinoids could serve as ligands for the RARs expressed at those stages. In addition, they could have a direct or indirect role in regulating RAR gene expression itself As an approach, a sensitive bioassay was used that has been previously used to estimate endogenous retinoid levels in other developing tissues and organs in chick and mouse embryos (Wagner et al., *Development* 116, 55–66 (1992); McCaffery et al., *Development* 115, 371–382(1992)). This bioassay utilizes an F9 teratocarcinoma cell line stably transfected with a retinoid-sensitive RARE/β-galactosidase reporter construct.

The entire cartilaginous humerus was microsurgically isolated from Day 5.5 (stage 27–28) embryos and the metaphyseal-diaphyseal portion of humerus from Days 8.5 and 10 chick embryos. The cartilaginous tissue was then carefully separated from the surrounding perichondrial tissues and the cartilaginous tissue processed for retinoid analysis. For comparison, the perichondrial tissues themselves were processed for analysis as well as liver, brain, eye and skin from the same Day 5.5, 8.5 and 10 embryos. Perichondrial tissues from Day 5.5 embryos, however, were excluded from analysis because they could not be obtained in sufficient quantities given the small size of the embryos. One hundred to 200 mg of each tissue or organ were suspended in fresh complete culture medium, homogenized and extracted; after clarification, the extracts were added to semiconfluent cultures of reporter F9 cells grown in 12 well plates. Cultures were reincubated for 24 hr and were then processed for histochemical detection of β-galactosidase activity. Negative control wells received mock-extracted fresh complete medium; positive control wells received fresh medium containing known amounts of all-trans-RA.

It was found that the cartilaginous tissues contained agents capable of stimulating transcription of the RAR reporter gene and did so at each stage of development examined. The amounts of retinoids in cartilage tissue extracts were much lower than those in liver, eye and skin as to be expected on the basis of the large quantities of retinoids present in these organs, but were higher than those present in brain extracts. Strikingly, it was also found that perichondrial tissues displayed extremely large amounts of retinoids. Negative and positive controls gave predictable results; F9 cells receiving vehicle alone (95% ethanol) were negative, while cells treated with 3 nM all-trans-RA were positive.

Retinoid Antagonists Derange Skeletal Development in Vivo

Having shown that RAR gene expression changes during chondrocyte maturation and that the cartilaginous elements as well as their surrounding perichondrial tissues contain endogenous retinoids, experiments were carried out to determine what roles the RARs and their ligands may play during chondrocyte maturation and skeletogenesis (see Example I, Antagonist Treatment). To approach this question, a bead containing retinoid antagonists was implanted in the vicinity of the prospective humeral mesenchymal condensation in stage 21–22 (Day 3–3.5) chick embryos and determined whether humerus development had been impaired by Day 10 in vivo. A bead containing Ro 41-5253 or AGN 109 at concentrations ranging from 3.5 μM to 3.5 mM was placed in one wing bud; the contralateral wing bud received a bead containing vehicle alone and served as control.

Both antagonists had striking effects on humerus development. The humerus of Day 10 embryos implanted with a Ro 41-5253-containing bead was about 50% shorter than control contralateral humerus treated with vehicle alone or untreated humerus. The effects were highly selective and topographically limited to the humerus; no obvious changes in size and/or shape were observed in the developing radius, ulna and digits. Similar effects were exerted by AGN 109, but much lower concentrations of this antagonist were required to obtain high frequency of humeral defects, possibly because of its ability to antagonize every RAR equally well (See Table I).

TABLE I

Dose-dependent effects of retinoid antagonists on humerus development

| Chick embryo Days | Treatment/Dose | n* | % Normal limbs | % Limbs with shortened humerus** |
| --- | --- | --- | --- | --- |
| 21–22 | none | 7 | 100 | 0 (0/7) |
| 21–22 | Ro 3.5 μM | 8 | 75 | 25 (2/8) |
| 21–22 | Ro 3.5 μM | 9 | 33 | 67 (6/9) |

TABLE I-continued

Dose-dependent effects of retinoid antagonists on humerus development

| Chick embryo Days | Treatment/Dose | n* | % Normal limbs | % Limbs with shortened humerus** |
|---|---|---|---|---|
| 21–22 | AGN 3.5 µM | 10 | 60 | 40 (4/10) |
| 21–22 | AGN 3.5 µM | 6 | 0 | 100 (6/6)*** |

*Total number of embryos used. Note that control embryos (indicated as "none") were implanted with a control bead filled with vehicle alone.
**Humerus was considered affected if it was at least 25% shorter than control.
***Two of these embryos had a shortened ulna or radius also.

Histological and in situ hybridization analyses of longitudinal sections of Day 10 humeri provided further details of the effects of the antagonists. In control humeri the epiphyses and metaphyses were well developed, and the diaphysis contained numerous maturing hypertrophic chondrocytes expressing RARγ and type X collagen, displayed a central core region undergoing replacement by bone and marrow and strongly expressing osteopontin and was surrounded by a thin intramembranous bony collar also expressing osteopontin.

In sharp contrast, the diaphysis of antagonist-treated humeri contained only small-sized chondrocytes expressing neither RARγ nor osteopontin and type X collagen, was completely cartilaginous, and had not undergone endochondral ossification nor marrow invasion. Interestingly, however, the diaphysis was surrounded by a seemingly normal intramembranous bone collar that expressed osteopontin, and the metaphyseal portions displayed Ihh gene expression as seen in control. It is also interesting to note that antagonist-treated humeri often displayed a curvature, with the concave side facing the antagonist-filled bead and the convex side facing the opposite side. No such curvature was observed in control humeri implanted with vehicle-filled bead. The effects elicited by the antagonists were limited to the humerus while skeletal elements distant from the site of bead implantation were normal in both morphology and gene expression, as exemplified by strong type X collagen gene expression in the ulnae of control and antagonist-implanted wings This reiterated the conclusion above that the inhibitory effects exerted by the retinoid antagonists were limited to the site of bead implantation and did not reflect generalized systemic effects.

In the next set of experiments, the issue was addressed whether antagonist treatment initiated at later stages of development would still lead to inhibition of humerus development. If so, this would correlate well with bioassay data showing that endogenous retinoids are continuously present in the cartilaginous tissues and suggesting that retinoids may be continuously required for skeletal development. The treatment period was also shortened as to minimize the interval between experimental manipulation and analysis of the effects. Thus, a single or multiple AGN 109-filled beads were implanted on one side or around the cartilaginous humerus in Day 5.5 (stage 28) chick embryos and the effects examined on Day 8.5. It was found that humerus development had been inhibited even after such short treatment timefrarne when implanted with 3–4 beads (6/7); a single bead was not very effective (5/5). Compared to their normal counterparts, the antagonist-treated humeri were shorter, and their cells had not advanced to the hypertrophic stage and lacked transcripts encoding RARγ and type X collagen. Both control and treated humeri exhibited very strong expression of type II collagen, indicating that the antagonist was not exerting unwanted side effects on cell viability and differentiated functions.

These experiments produced two additional interesting data. The first one was that in control Day 8.5 humerus the first type X collagen-expressing chondrocytes emerged at the periphery of the diaphysis. This data is in perfect agreement with morphological observations above and was confirmed by in situ hybridization on serial sections throughout the diaphysis. The second interesting data was that the antagonist-treated humeri were morphologically straight as the controls and never displayed a curvature, possibly because the antagonist-filled beads had been placed on both sides of the humeri.

To determine whether the effects of antagonist treatment were reversible and would dissipate with time and further development, embryos implanted with AGN 109 beads at stage 28 (Day 5.5) as above were allowed to develop until Days 14 to 18 of embryogenesis and were then processed for histology and in situ hybridization. It was found that by Day 14 the antagonist-treated humeri contained hypertrophic chondrocytes in their diaphysis exhibiting characteristic gene expression patterns, that is strong type X collagen and low type II collagen gene expression. In addition, bone and bone marrow progenitor cells had begun to invade the hypertrophic cartilage. These morphological and gene expression features normally characterize the humerus around Day 9–9.5 of embryogenesis, indicating that development of antagonist-treated humerus had been delayed by about 5 days but was now resuming its normal course.

Cultured Chondrocytes

In a final set of studies, it was determined whether the antagonists used in the above in vivo experiments are able to antagonize the biological effects of natural retinoids in chondrocytes and whether the antagonists were able to block or inhibit the pro-maturation effects of exogenous all-trans-RA on cultures of chick embryo chondrocytes (see Example I, Chondroycte Cultures). As shown previously, cultures of immature chondrocytes isolated from the caudal resting portion of Day 17–18 chick embryo sternum require treatment with all-trans-RA to develop into hypertrophic type X collagen-expressing cells. Likewise, cultures of newly-emerged hyper- trophic chondrocytes isolated from the cephalic portion of Day 17–18 chick embryo sternum require all-trans-RA treatment to complete their maturation into post-hypertrophic alkaline phosphatase-rich, mineralizing chondrocytes (Pacifici et al., *Exp. Cell Res.* 195, 38–46 (1991); Iwamoto et al., *Exp. Cell Res.* 207, 413–420 (1993b); *Microsc. Res. Tech.* 28,483–491 (1994)).

Thus, immature caudal sternal chondrocytes were grown in standard serum containing cultures for about 2 weeks. During this period, the cells actively proliferated and increased moderately in size (about 2–3 fold), indicating that they had advanced to a pre-hypertrophic stage of maturation (see Pacifici et al., *Exp. Cell Res.* 195, 38–46 (1991)). Cultures were then treated with all-trans-RA, Ro 41-5253, both all-trans-RA and Ro 41-5253, or left untreated. Northern blot analysis showed that control untreated cultures contained barely detectable amounts of type X collagen transcripts;. However, cultures treated for 2, 4 or 6 days with 50 nM all-trans-RA displayed a marked time-dependent increase in type X collagen transcripts. Such increase was significantly, though not totally, blocked by co-treatment with 500 nM Ro 41-5253. Treatment with antagonist alone did not have major effects. Thus, Ro 41-5253 is able to counteract the up-regulation of an early maturation marker, type X collagen, in cultured pre-hypertrophic caudal sternal chondrocytes.

This conclusion was confirmed and extended with cultures of more mature chondrocytes isolated from the cephalic core portion of sternum. Two week-old control untreated cultures displayed the expected hypertrophic cell phenotype characterized by a large cell diameter (see Pacifici et al., *Exp. Cell Res.* 195, 38–46 (1991)) and abundant type X collagen mRNA. When the cells were treated with 50 nM all-trans-RA, gene expression of the late maturation marker alkaline phosphatase was increased dramatically, while expression of type X collagen was essentially eliminated by 6 days of treatment, in excellent correlation with the fact that alkaline phosphatase expression is up-regulated and type X collagen expression is down-regulated in vivo when hypertrophic chondrocytes advance to their terminal post-hypertrophic mineralizing stage during endochondral ossification (Iwamoto et al., *Micros. Res. Tech.* 28, 483–491 (1994)). The opposite responses of these two genes to all-trans-RA treatment were counteracted by co-treatment with 500 nM Ro 41-5253. Thus, alkaline phosphatase gene expression remained quite low while type X collagen gene expression remained fairly strong. Treatment with antagonist alone had no major effects. Similar data were obtained with AGN 109.

To examine the mineralizing stage of the chondrocyte maturation process, maturing chondrocytes isolated from the cephalic core portion of sternum were grown for 2 weeks in 22 mm multiwell plates until confluent and were then treated for 6 days with all-trans-RA, both all-trans-RA and Ro 41-5253, or Ro 41-5253 alone. All cultures received β-glycerophosphate, a phosphate donor needed for mineral formation and deposition; mineral was revealed by staining with alizarin red. Control untreated cultures exhibited no detectable staining. In contrast, cultures treated with 25 or 50 nM all-trans-RA contained abundant alizarin red-stainable mineral. Increasing amounts of Ro 41–5253 did effectively antagonize the pro-mineralization effects of all-trans-RA such that cultures co-treated with 25 or 50 nM all-trans-RA and 500 nM Ro 41-5253 exhibited almost no mineralization. Treatment with Ro 41-5253 alone had no effects.

Thus, exogenous all-trans-RA induces changes in gene expression, cell behavior and activities in cultured sternal chondrocytes which are identical to those occurring at the different stages of chondrocyte maturation in vivo. The retinoid antagonists used counteract the pro-maturation abilities of all-trans-RA.

We claim:
1. A method for treating a cartilage or bone pathology characterized by endochondral ossification, the method comprising administering a therapeutically effective amount of an RAR receptor antagonist.
2. The method of claim 1, wherein said pathology is osteoarthritis.
3. A method according to claim 1, wherein the antagonist is a compound of formula (I):

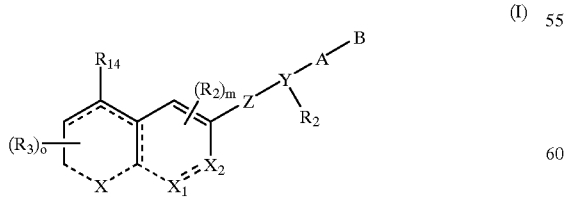

(I)

wherein
X is S, SO, $SO_2$, O, $NR_1$ or $[C(R_1)_2]_n$ where each $R_1$ is independently H or alkyl of 1 to 6 carbons, and n is 1 or 2;

or X is absent;

$X_1$ and $X_2$ are each C; or $X_1$ is absent and $X_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

provided that at least X is present, or $X_1$ and $X_2$ are each C;

- - - is an optionally present bond;

each $R_2$ is independently or together hydrogen, lower alkyl of 1 to 6 carbons, F, Cl, Br, I, $CF_3$, fluoro substituted alkyl of 1 to 6 carbons, OH, SH, alkoxy of 1 to 6 carbons, alkylthio of 1 to 6 carbons, $NH_2$, $NR_1H$, $N(R_1)_2$, $N(R_1)COR_1$, $NR_1CON(R_1)_2$ or $OCOR_1$;

each $R_3$ is independently or together hydrogen, lower alkyl of 1 to 6 carbons, F, Cl, Br or I;

m is an integer having a value of 0–3;

o is an integer having a value of 0–3;

Z is —C C—, —N=N—, —N=$CR_1$—, —$CR_1$=N—, —$(CR_1=CR_1)_{n'}$— where n' is an integer having a value of 0–5,
—$CONR_1$—,
—$CSNR_1$—,
—$NR_1CO$—,
—$NR_1CS$—,
—COO—,
—OCO—,
—CSO— or
—OCS—

Y is a phenyl or naphthyl group, or heteroaryl selected from the group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is —$(CR_1=CR_1)_{n'}$— and n' is 3, 4 or 5 then Y represents a direct valence bond between said —$(CR_1=CR_1)_{n'}$ group and B;

A is $(CH_2)_q$ where q is 1–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds; or A is a direct bond or is absent;

B is hydrogen, COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or trilower alkylsilyl, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons; and $R_{14}$ is $(R_{15})_r$-phenyl, $(R_{15})_r$-naphthyl, or $(R_{15})_r$-heteroaryl where the heteroaryl group has 1 to 3 heteroatoms selected from the group consisting of O, S and N, r is an integer having the values of 0–6, and $R_{15}$ is independently H, F, Cl, Br, I, $NO_2$, $N(R_8)_2$, $N(R_8)COR_8$, $NR_8 CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or (trialkylsilyl)oxy group where the alkyl groups independently have 1 to 6 carbons; or a pharmaceutically acceptable salt or ester thereof.

4. A method according to claim 1, wherein the antagonist is a compound of formula (I):

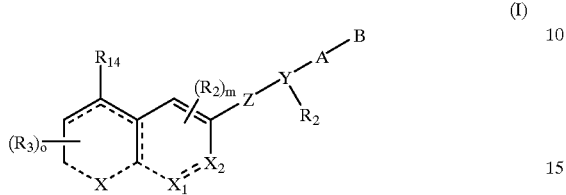

wherein

X is S, SO, $SO_2$, O, $NR_1$ or $[C(R_1)_2]_n$ where each $R_1$ is independently H or alkyl of 1 to 6 carbons, and n is 1 or 2;

or X is absent;

$X_1$ and $X_2$ are each C; or $X_1$ is absent and $X_2$ is hydrogen, lower aklyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

provided that at least X is present, or $X_1$ and $X_2$ are each C;

- - - is an optionally present bond;

each $R_2$ is independently or together hydrogen, lower alkyl of 1 to 6 carbons, F, Cl, Br, I, $CF_3$, fluoro substituted alkyl of 1 to 6 carbons, OH, SH, alkoxy of 1 to 6 carbons, alkylthio of 1 to 6 carbons, $NH_2$, $NR_1H$, $N(R_1)_2$, $N(R_1)COR_1$, $NR_1CON(R_1)_2$ or $OCOR_1$;

each $R_3$ is independently or together hydrogen, lower alkyl of 1 to 6 carbons, F, Cl, Br or I;

m is an integer having a value of 0–3;

o is an integer having a value of 0–3;

Z is —C≡C—, —N=N—, —N=$CR_1$—, —$CR_1$=N—, —($CR_1$=$CR_1$)$_{n'}$— where n' is an integer having a value of 0–5,

—$CONR_1$—,

—$CSNR_1$—,

—$NR_1CO$—,

—$NR_1CS$—,

—COO—,

—OCO—,

—CSO— or

—OCS—

Y is a phenyl or naphthyl group, or heteroaryl selected from the group consisting of pyridyl, thienyl, frlyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is —($CR_1$=$CR_1$)$_{n'}$ and n' is 3, 4 or 5 then Y represents a direct valence bond between said —($CR_1$=$CR_1$)$_{n'}$ group and B;

A is $(CH_2)_q$ where q is 1–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds; or A is a direct bond or is absent;

B is hydrogen, COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkysilyl, where $R_7$ is an alkyl, cycloalkyl or alkenyl group containing 1 to 5 carbons, $R_8$ is an alkyl group of 1 to 10 carbons or (triretylsilyl)allyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower awylphenyl, $R_{11}$ is lower alkyl, phenyl or lower alkylphenyl, $R_{12}$ is lower alkyl, and $R_{13}$ is divalent alkyl radical of 2–5 carbons; and $R_{14}$ is $(R_{15})_r$-phenyl, $(R_{15})_r$-naphthyl, or $(R_{15})_r$-heteroaryl where the heteroaryl group has 1 to 3 heteroatoms selected from the group consisting of O, S and N, r is an integer having the values of 0–6, and $R_{15}$ is independently H, F, Cl, Br, I, $NO_2$, $N(R_8)_2$, $N(R_8)COR_8$, $NR_8 CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or (trialkylsilyl)oxy group where the alkyl groups independently have 1 to 6 carbons; or a pharmaceutically acceptable salt or ester thereof.

5. The method of claim 4, wherein X is present and $X_1$ is absent.

6. The method of claim 5, wherein Y is phenyl and $R_{14}$ is $(R_{15})_r$-phenyl.

7. The method of claim 6, wherein Y($R_2$)—A—B is -phenyl-COOH.

8. The method of claim 4, wherein X is absent and $X_1$ and $X_2$ are C.

9. The method of claim 8, wherein Y is phenyl and $R_{14}$ is $(R_{15})_r$-phenyl.

10. The method of claim 9, wherein Y$R_2$)—A—B is -phenyl-COOH.

11. The method of claim 4, wherein X is present and $X_1$ and $X_2$ are C.

12. The method of claim 11, wherein Y is phenyl and $R_{14}$ is $(R_{15})_r$-phenyl.

13. The method of claim 12, wherein Y($R_2$)—A—B is -phenyl-COOH.

14. The method of claim 13, wherein the compound is

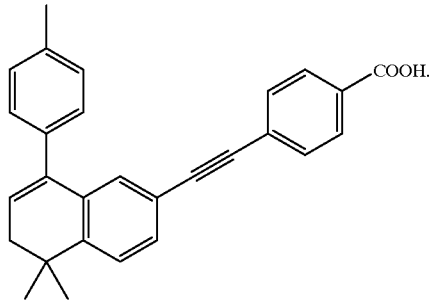

15. A method according to claim 1, wherein the antagonist is a compound of formula (II):

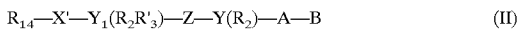

where $R_{14}$ is $R_{15})_r$-phenyl, $(R_{15})_r$-naphthyl or $(R_{15})_r$-heteroaryl where the heteroaryl group has 1 to 3 heteroatoms selected from the group consisting of O, S and N, r is an integer having a value of 0–6, and $R_{15}$ is independently H, F, Cl, Br, I, $NO_2$, $N(R_8)_2$, $N(R_8)COR_8$, $NR_8 CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or (trialkylsilyl)oxy group where the alkyl groups independently have 1 to 6 carbons;

X' is O, S, SO, $SO_2$, N, $NR_3$ or $C(R_3)_2$; or —X'—$R_{14}$ is —$C(R_{14})H_2$ or —$C(R_{14})$—$(CH_2)_n$H where n is 1–6;

$Y_1$ is phenyl, naphthyl or heteroaryl selected from the group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being optionally substituted with one R'$_3$ and one or two $R_2$ groups;

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, alkylthio of 1 to 6 carbons, $NH_2$, $NR_1H$, $N(R_1)_2$, $N(R_1)COR_1$, $NR_1CON(R_1)_2$ or $OCOR_1$;

R'$_3$ is H, ($C_1$-$C_{10}$) alkyl, 1-adamantyl, 2-tetrahydropyranoxy, trialkylsilanyl and trialkylsilanyloxy where alkyl comprises 1 to 6 carbons, alkoxy and alkylthio where alkyl comprises 1 to 10 carbons, or $OCH_2O(C_{1-6})$alkyl;

Z is —C C—, —N=N—, —N=$CR_1$—, —$CR_1$=N—, —($CR_1$=$CR_1$)$_{n'}$— where n' is an integer having a value of 0–5,
—$CONR_1$—,
—$CSNR_1$—,
—$NR_1CO$—,
—$NR_1CS$—,
—COO—,
—OCO—,
—CSO— or
—OCS— where each $R_1$ is independently or together H or alkyl of 1 to 6 carbons, and n is 1 or 2;

Y is a phenyl or naphthyl group, or heteroaryl selected from the group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is —($CR_1$=$CR_1$)$_{n'}$— and n' is 3, 4 or 5 then Y represents a direct valence bond between said —($CR_1$=$CR_1$)$_{n'}$ group and B;

A is $(CH_2)_q$ where q is 1–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds; or A is a direct bond or is absent; and B is hydrogen, COOH, $COO_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkyls, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons; or a pharmaceutically acceptable salt or ester thereof.

16. The method according to claim 15, wherein the antagonist is a compound of formula (IIa):

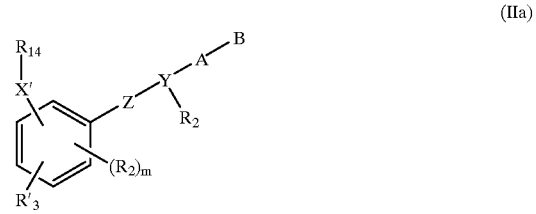

(IIa)

where m is 0–2.

17. The method according to claim 15, wherein the antagonist is a compound of formula (IIb):

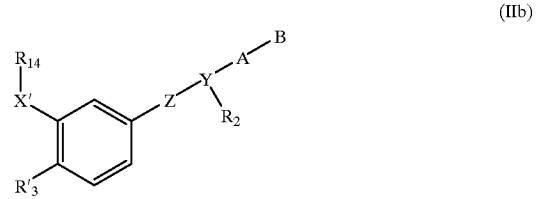

(IIb)

where R'$_3$ is alkyl.

18. A method according to claim 15, wherein the antagonist is a compound of formula (IIc):

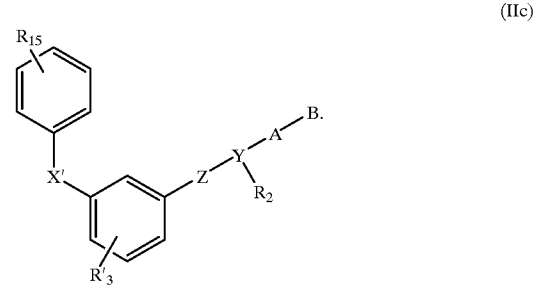

(IIc)

19. A method according to claim 1, wherein the antagonist is a compound of formula (III):

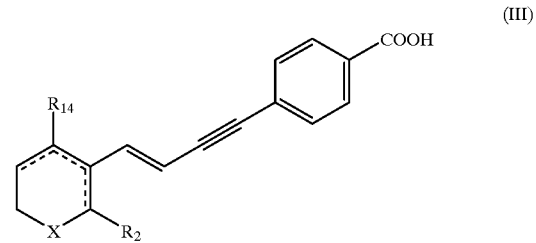

(III)

wherein
X is S, SO, $SO_2$, O, $NR_1$ or $[C(R_1)_2]_n$ where each $R_1$ is independently or together H or alkyl of 1 to 6 carbons, and n is 1 or 2;

$R_2$ is $C_1$–$C_6$ alkenyl; and $R_{14}$ is $(R_{15})_r$-phenyl, $(R_{15})_r$-naphthyl, or $(R_{15})_r$-heteroaryl where the heteroaryl group has 1 to 3 heteroatoms selected from the group consisting of O, S and N, r is an integer having the values of 0–6, and $R_{15}$ is independently H, F, Cl, Br, I, $NO_2$, $N(R_8)_2$, $N(R_8)COR_8$, $NR_8 CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or (trialkylsilyl)oxy group where the alkyl groups independently have 1 to 6 carbons, where $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl; or a pharmaceutically acceptable salt or ester thereof.

20. A method according to claim 1, wherein the antagonist is a compound of the formula (IV):

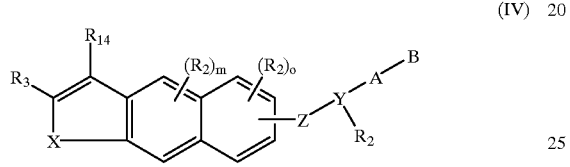

(IV)

wherein

X is S, SO, $SO_2$, O, $NR_1$, $[C(R_1)_2]_n$, —$C(R_8)_2$—$NR_1$—, —$C(R_1)_2$—S—, —$C(R_1)_2$—O— or —$C(R_1)_2$—$(R_1)_2$—, where each $R_1$ is independently or together H or alkyl of 1 to 6 carbons, and n is 1 or 2;

each $R_2$ is independently or together hydrogen, lower alkyl of 1 to 6 carbons, F, Cl, Br, I, $CF_3$, fluoro substituted alkyl of 1 to 6 carbons, OH, SH, alkoxy of 1 to 6 carbons, alkylthio of 1 to 6 carbons, $NH_2$, $NR_1H$, $N(R_1)_2$, $N(R_1)COR_1$, $NR_1CON(R_1)_2$ or $OCOR_1$;

$R_3$ is hydrogen, lower alkyl of 1 to 6 carbons, F, Cl, Br or I;

m is an integer having the value of 0–3;

o is an integer having the value of 0–3;

Z is —C C—, —N=N—, —N=$CR_1$—, —$CR_1$=N, —$(CR_1=CR_1)_{n'}$— where n' is an integer having the value 0–5,
—$CONR_1$—,
—$CSNR_1$—,
—$NR_1CO$—,
—$NR_1CS$—,
—COO—,
—OCO—;
—CSO—;
—OCS—;

Y is a phenyl or naphthyl group, or heteroaryl selected from the group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is —$(CR_1=CR_1)_{n'}$— and n' is 3, 4 or 5 then Y represents a direct valence bond between said —$(CR_1=CR_1)_{n'}$ group and B;

A is $(CH_2)_q$ where q is 1–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds; or A is a direct bond or is absent;

B is hydrogen, COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons; and $R_{14}$ is $(R_{15})_r$-phenyl, $(R_{15})_r$-naphthyl, or $(R_{15})_r$-heteroaryl where the heteroaryl group has 1 to 3 heteroatoms selected from the group consisting of O, S and N, r is an integer having a value of 0–6, and $R_{15}$ is independently H, F, Cl, Br, L $NO_2$, $N(R_8)_2$, $N(R_8)COR_8$, $NR_8 CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or (trialkylsilyl)oxy group where the alkyl groups independently have 1 to 6 carbons; or a pharmaceutically acceptable salt or ester thereof.

21. A method according to claim 1, wherein the antagonist is a compound of formula (V):

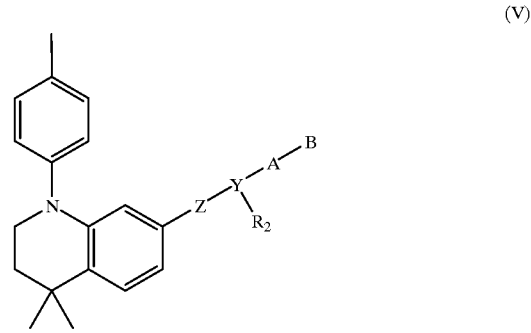

(V)

wherein

Z is —C C—, —N=N—, —N=$CR_1$—, —$CR_1$=N, —$(CR_1=CR_1)_{n'}$— where n' is an integer having the value 0–5,
—$CONR_1$—,
—$CSNR_1$—,
—$NR_1CO$—,
—$NR_1CS$—,
—COO—,
—OCO—;
—CSO—;
—OCS—;

where each $R_1$ is independently or together H or alkyl of 1 to 6 carbons, and n is 1 or 2;

Y is a phenyl or naphthyl group, or heteroaryl selected from the group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is —$(CR_1=CR_1)_{n'}$— and n' is 3, 4 or 5 then Y represents a direct valence bond between said —$(CR_1=CR_1)_{n'}$ group and B;

A is $(CH_2)_q$ where q is 1–5, lower branched chain alkl having 3–6 carbons, cycloalkyl having 3–6 carbons, alkenyl having 2–6 carbons and 1 or 2 double bonds, alkynyl having 2–6 carbons and 1 or 2 triple bonds; or A is a direct bond or is absent;

B is hydrogen, COOH, $COOR_8$, $CONR_9R_{10}$, —$CH_2OH$, $CH_2OR_{11}$, $CH_2OCOR_{11}$, CHO, $CH(OR_{12})_2$, $CHOR)_{13}O$, —$COR_7$, $CR_7(OR_{12})_2$, $CR_7OR_{13}O$, or tri-lower alkylsilyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alky, phenyl or lower alkylphenyl, $R_{12}$ is lower alkyl, and $R_{13}$ is divalent alkyl radical of 2–5 carbons; and $R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, alkylthio of 1 to 6 carbons, $NH_2$, $NR_1H$, $N(R_1)_2$, $N(R_1)COR_1$, $NR_1CON(R_1)_2$ or $OCOR_1$; or a pharmaceutically acceptable salt or ester thereof.

22. The method of claim 1 wherein said RAR antagonist is a compound of formula (VI):

wherein

X is S, O, NR' where R' is H or allyl of 1 to 6 carbons, or X is $[C(R_1)_2]_n$ where $R_1$ is independently H or alkyl of 1 to 6 carbons, and n is an integer having a value of 0–2;

$R_2$ is independently hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R_3$ is independently hydrogen, lower alkyl of 1 to 6 carbons or F;

m is an integer having the value of 0–3;

o is an integer having the value of 0–3;

Y is a phenyl or naphthyl group, or heteroaryl selected from a group consisting of pyridyl, thienyl, fuiryl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds; or A is a direct bond or is absent;

B is hydrogen, COOH or a pharmaceutically acceptable salt thereof, $COO_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons;

$R_{14}$ is $(R_{15})_r$-phenyl, $(R_{15})_r$-naphthyl, or $(R_{15})_r$-heteroaryl where the heteroaryl group has 1 to 3 heteroatoms selected from the group consisting of O, S and N, r is an integer having a value of 0–5;

$R_{15}$ is independently H, F, Cl, Br, I, $NO_2$, $N(R_8)_2$, $N(R_8)COR_8$, $NR_8CON(R_8)_2$, OH, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons;

$R_{16}$ is H, lower alkyl of 1 to 6 carbons;

$R_{17}$ is H, lower alkyl of 1 to 6 carbons, OH or $OCOR_{11}$;

p is zero or 1, with the proviso that when p is 1 then $R_{17}$ is absent; and m is an integer from 0–2.

23. The method of claim 1 wherein said RAR antagonist is a compound of formula (VII):

where

X is $C(R_1)_2$ or O;

$R_1$ is H or alkyl of 1 to 6 carbons;

$R_2$ is independently lower alkyl of 1 to 6 carbons, F, Cl, Br, 1, $CF_3$, fluoro substituted alkyl of 1 to 6 carbons, OH, SH, alkoxy of 1 to 6 carbons, or alkylthio of 1 to 6 carbons;

m is an integer having a value of 0–3;

$R_3$ is independently lower alkyl of 1 to 6 carbons or F;

o is an integer having a value of 0–3;

s is an integer having a value of 1–3;

$R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl;

$R_{15}$ is independently H, F, Cl, Br, I, $NO_2$, $N(R_8)_2$, $COR_8$, $NR_8CON(R_8)_2$, $OCOR_8$, $OR_8$, CN an alkyl group having 1 to 10 carbons, fluoro substituted alkyl group having 1 to 10 carbons, an alkenyl group having 1 to 10 carbons and 1 to 3 double bonds, an alkynyl group having 1 to 10 carbons and 1 to 3 triple bonds, or a trialkylsilyl or trialkylsilyloxy group where the alkyl groups independently have 1 to 6 carbons; and t is an integer having a value of 0–5, where the CONH group is in the 6 or 7 position of the benzopyran, and in the 2 or 3 position of the dihydronaphtbaline ring, or a pharmaceutically acceptable salt thereof.

24. The method of claim 1 wherein said RAR antagonist of the formula (VII):

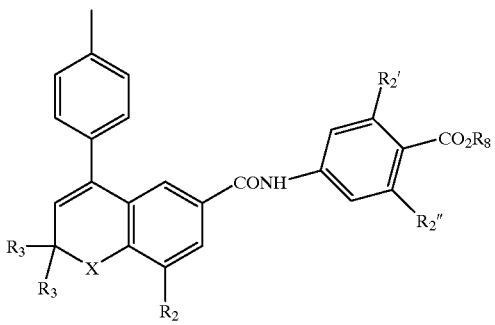

where

X is $C(CH_3)_2$ or O, and;

$R_2$ is H or Br;

$R_{2'}$ and $R_{2''}$, independently are H or F;

$R_3$ is H or $CH_3$; and $R_8$ is H, lower alkyl of 1 to 6 carbons, or a pharmaceutically acceptable salt of said compound.

25. The method of claim 1 wherein said RAR antagonist is of the formula (IX):

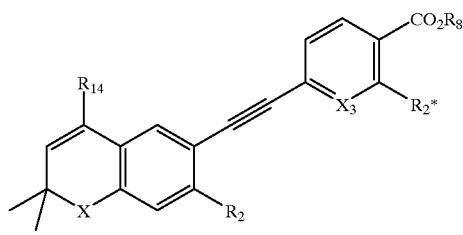

where

X is S or O;

$X_3$ is CH or N;

$R_2$ is H, F, $CF_3$ or alkoxy of 1 to 6 carbons;

$R_2^*$ is H, F or $CF_3$;

$R_8$ is H or lower alkyl of 1 to 6 carbons; and $R_{14}$ is unsubstituted phenyl, thienyl or pyridyl, or phenyl, thienyl or pyridyl substituted with one to three $R_{15}$ groups, where $R_{15}$ is lower alkyl of 1 to 6 carbons, chlorine, $CF_3$ or alkoxy of 1 to 6 carbons;

or a pharmaceutically acceptable salt thereof.

26. The method of claim 25 wherein X is S;

$R_2$ is H, F or $OCH_3$;

$R_2^*$ is H or F; and $R_{14}$ is selected from the group consisting of phenyl, 4-(lower-alkyl)phenyl, 5-(lower alkyl)-2-thienyl, and 6-(lower alkyl)-3-pyridyl where lower alkyl has 1 to 6 carbons; or a pharmaceutically acceptable salt thereof.

27. The method of claim 25 wherein X is O;

$X_3$ is CH;

$R_2$ is H;

$R_2^*$ is H or F; and $R_{14}$ is selected from the group consisting of phenyl and 4-(lower-alkyl)phenyl, where lower alkyl has 1 to 6 carbons;

or a pharmaceutically acceptable salt thereof.

28. The method of claim 26 wherein $X_3$ is CH; $R_2$ is H; $R_2^*$ is H; and $R_{14}$ is ethyl;

or a pharmaceutically acceptable salt thereof.

29. The method of claim 1 wherein the RAR antagonist is of formula (X):

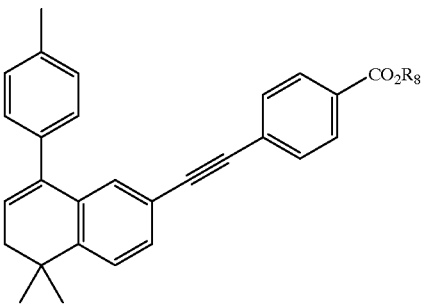

where $R_8$ is H or lower alkyl of 1 to 6 carbons;

or a pharmaceutically acceptable salt thereof.

30. The method of claim 1 wherein said RAR antagonist is:

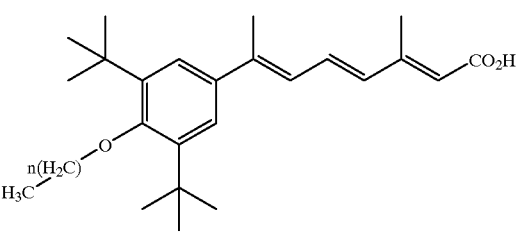

where is an integer from 1 to 10;

or a pharmaceutically acceptable salt thereof.

31. The method of claim 1 wherein said RAR antagonist is:

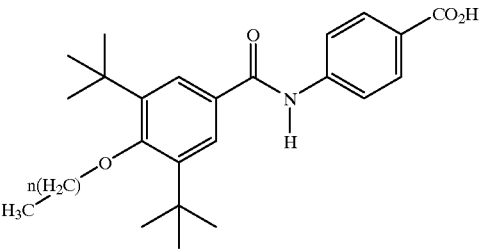

where n is an integer from 1 to 10; or a pharmaceutically acceptable salt thereof.

32. The method of claim 1 wherein said RAR antagonist is:

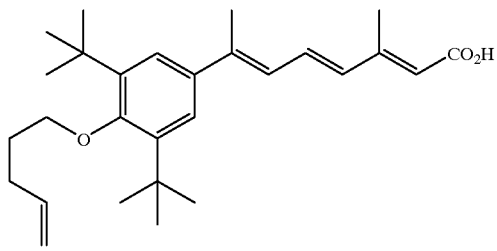

or a pharmaceutically acceptable salt thereof.

33. The method of claim 1 wherein said RAR antagonist is:

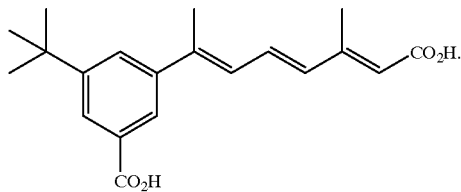

34. The method of claim 1 wherein said RAR antagonist is:

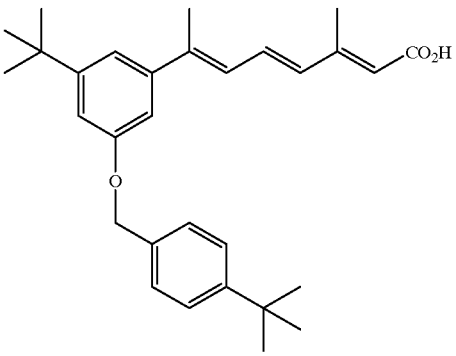

or a pharmaceutically acceptable salt thereof.

35. A method for treating a cartilage or bone pathology, the method comprising antagonizing RARγ receptors associated with said pathology.

36. The method of claim 35, wherein said pathology is osteoarthritis.

37. A method for ameliorating the symptoms associated with a cartilage or bone pathology characterized by endochondrial ossification, the method comprising administering a therapeutically effective amount of a retinoid receptor antagonist.

38. The method of claim 37, wherein said retinoid receptor antagonist is an RAR receptor antagonist.

39. The method of claim 37, wherein said RAR receptor antagonist is an RARαβγ receptor antagonist.

40. The method of claim 37, wherein said pathology is osteoarthritis.

41. A method for treating for treating a cartilage or bone pathology characterized by endochondrial ossification comprising administering a therapeutically effective amount of a pharmaceutical composition comprising an RAR antagonist and a pharmaceutically acceptable carrier or excipient.

42. The method of claim 41, wherein said pathology is osteoarthritis.

* * * * *

UNITED STATES PATENT AND TRADEMARK OFFICE
CERTIFICATE OF CORRECTION

PATENT NO.   : 6,313,168 B1
DATED        : November 6, 2001
INVENTOR(S)  : Pacifici et al.

It is certified that error appears in the above-identified patent and that said Letters Patent is hereby corrected as shown below:

Column 5,
Line 37, delete "NR1-" and insert in place thereof -- $NR_1$- --

Column 14,
Line 9, delete "Adosage" and insert in place thereof -- dosage --

Column 15,
Line 17, delete "α12" and insert in place thereof -- α2 --

Column 16,
Line 18, delete "3846" and insert in place thereof -- 38-46 --
Line 19, delete "413420" and insert in place thereof -- 413-420 --

Column 17,
Line 38, delete "$RXR_8$" and insert in place thereof -- RXRs --

Column 18,
Line 45, delete "15"

Column 19,
Line 5, delete "413420" and insert in place thereof -- 413-420 --
Line 31, delete "RARβ" and insert in place thereof -- RARs --
Line 47, after "itself" insert -- . --

Column 21,
Line 62, delete "timefrarne" and insert in place thereof -- timeframe --

Column 22,
Line 9, delete "confirned" and insert in place thereof -- confirmed --

Column 25,
Line 55, delete "frlyl" and insert in place thereof -- furyl --

Column 26,
Line 6, delete "trirethylsilyl" and insert in place thereof -- trimethylsilyl --

UNITED STATES PATENT AND TRADEMARK OFFICE
CERTIFICATE OF CORRECTION

PATENT NO. : 6,313,168 B1
DATED : November 6, 2001
INVENTOR(S) : Pacifici et al.

It is certified that error appears in the above-identified patent and that said Letters Patent is hereby corrected as shown below:

Column 27,
Line 58, delete "$COO_8$" and insert in place thereof -- $COOR_8$ --
Line 61, delete "alkyls" and insert in place thereof -- alkylsilyl --

Column 31,
Line 1, delete "alkl" and insert in place thereof -- alkyl --
Line 52, delete "friuryl" and insert in place thereof -- furyl --
Line 63, delete "$C00_8$" and insert in place thereof -- $COOR_8$ --

Column 32,
Line 47, delete "1" and insert in place thereof -- I --

Column 33,
Line 25, delete "$R_2$'," and insert in place thereof -- $R_2$" --

Column 34,
Line 9, delete "pharnecutically" and insert in place thereof -- pharmaceutically --
Line 48, after "where" insert -- n is an integer from 1 to 10 --

Signed and Sealed this

Thirteenth Day of August, 2002

Attest:

JAMES E. ROGAN
Attesting Officer    Director of the United States Patent and Trademark Office